(12) United States Patent
Duncan et al.

(10) Patent No.: US 10,591,455 B2
(45) Date of Patent: Mar. 17, 2020

(54) MOBILE WATER ANALYSIS

(71) Applicant: Hach Company, Loveland, CO (US)

(72) Inventors: Jim Duncan, Longmont, CO (US);
Aria Farjam, Dusseldorf (DE); Jim Harbridge, Thornton, CO (US); Brian Harmon, Loveland, CO (US); Ulrich Lundgreen, Gutersloh (DE); Darren MacFarland, Windsor, CO (US); Leon Moore, Windsor, CO (US); Perry Palumbo, Fort Collins, CO (US); William Louis Pherigo, Jr., Loveland, CO (US); Robert Stoughton, Boulder, CO (US); Luke Waaler, Longmont, CO (US)

(73) Assignee: HACH COMPANY, Loveland, CO (US)

( * ) Notice: Subject to any disclaimer, the term of this patent is extended or adjusted under 35 U.S.C. 154(b) by 119 days.

(21) Appl. No.: 15/631,703

(22) Filed: Jun. 23, 2017

(65) Prior Publication Data

US 2017/0284990 A1   Oct. 5, 2017

Related U.S. Application Data

(60) Division of application No. 14/874,058, filed on Oct. 2, 2015, now Pat. No. 9,719,914, which is a
(Continued)

(51) Int. Cl.
*B01L 3/00* (2006.01)
*G01N 1/10* (2006.01)
(Continued)

(52) U.S. Cl.
CPC .............. *G01N 33/18* (2013.01); *B01L 3/508* (2013.01); *B01L 3/5027* (2013.01);
(Continued)

(58) Field of Classification Search
CPC ................................... B01L 3/00; G01N 1/10
(Continued)

(56) References Cited

U.S. PATENT DOCUMENTS 3,867,042 A   2/1975   Mayer
4,933,147 A   6/1990   Hollar
(Continued)

FOREIGN PATENT DOCUMENTS

EP   1764153 A2   3/2007
EP   2266691 A1   12/2010

OTHER PUBLICATIONS

Federal Public Service, Ministry of Industry, Foreign Trade and Services, Brazilian Patent and Trademark Office, Search Report, dated Dec. 2, 2019, pp. 4.

*Primary Examiner* — Brian J. Sines
(74) *Attorney, Agent, or Firm* — Ference & Associates LLC

(57) ABSTRACT

An embodiment provides a method, including: operating a motor to position sample fluid within a fluid channel of a cuvette; transmitting light through an optical chamber of the cuvette; measuring a value of received light that has been transmitted through the optical chamber; comparing the measured value of light to one or more thresholds; determining a position of the sample fluid within the fluid channel based on a comparison from the comparing step; and generating a response based upon the position of the sample fluid with the fluid channel. Other aspects are described and claimed.

10 Claims, 34 Drawing Sheets

Related U.S. Application Data continuation of application No. 13/844,153, filed on Mar. 15, 2013, now Pat. No. 9,180,449.

(60) Provisional application No. 61/723,174, filed on Nov. 6, 2012, provisional application No. 61/710,294, filed on Oct. 5, 2012, provisional application No. 61/710,282, filed on Oct. 5, 2012, provisional application No. 61/710,259, filed on Oct. 5, 2012, provisional application No. 61/658,753, filed on Jun. 12, 2012.

(51) Int. Cl.

| | | |
|---|---|---|
| *G01N 33/18* | (2006.01) | |
| *G01N 21/25* | (2006.01) | |
| *G01N 21/78* | (2006.01) | |
| *G01N 31/22* | (2006.01) | |
| *G01N 21/03* | (2006.01) | |
| *G01N 21/05* | (2006.01) | |
| *G01N 21/59* | (2006.01) | |

(52) U.S. Cl.
CPC ......... *B01L 3/502715* (2013.01); *B01L 3/545* (2013.01); *G01N 21/03* (2013.01); *G01N 21/0303* (2013.01); *G01N 21/05* (2013.01); *G01N 21/251* (2013.01); *G01N 21/59* (2013.01); *G01N 21/78* (2013.01); *G01N 31/22* (2013.01); *G01N 33/182* (2013.01); *B01L 2300/021* (2013.01); *B01L 2300/022* (2013.01); *B01L 2300/0654* (2013.01); *B01L 2300/0816* (2013.01); *B01L 2300/0883* (2013.01); *B01L 2300/12* (2013.01); *B01L 2300/1827* (2013.01); *B01L 2400/0487* (2013.01)

(58) Field of Classification Search
USPC ....... 422/502, 503, 504; 436/43, 52, 53, 180
See application file for complete search history.

(56) References Cited

U.S. PATENT DOCUMENTS

| | | |
|---|---|---|
| 5,571,396 A | 11/1996 | Cormier |
| 5,572,328 A | 11/1996 | Fouckhardt et al. |
| 6,596,237 B1 | 7/2003 | Borrelli et al. |
| 8,830,449 B1 | 9/2014 | Lamego |
| 2002/0033193 A1* | 3/2002 | McNeely .......... B01L 3/502738 137/825 |
| 2002/0079008 A1* | 6/2002 | Chien ............... B01L 3/502753 137/827 |
| 2005/0011761 A1* | 1/2005 | Chien ................. B01L 3/5027 204/450 |
| 2005/0013735 A1 | 1/2005 | Gebrian |
| 2005/0084426 A1 | 4/2005 | Mimura |
| 2006/0065361 A1* | 3/2006 | Stiene ............... B01L 3/502707 156/292 |
| 2006/0152999 A1 | 7/2006 | Dunfee |
| 2012/0021527 A1 | 1/2012 | Salzer et al. |

* cited by examiner

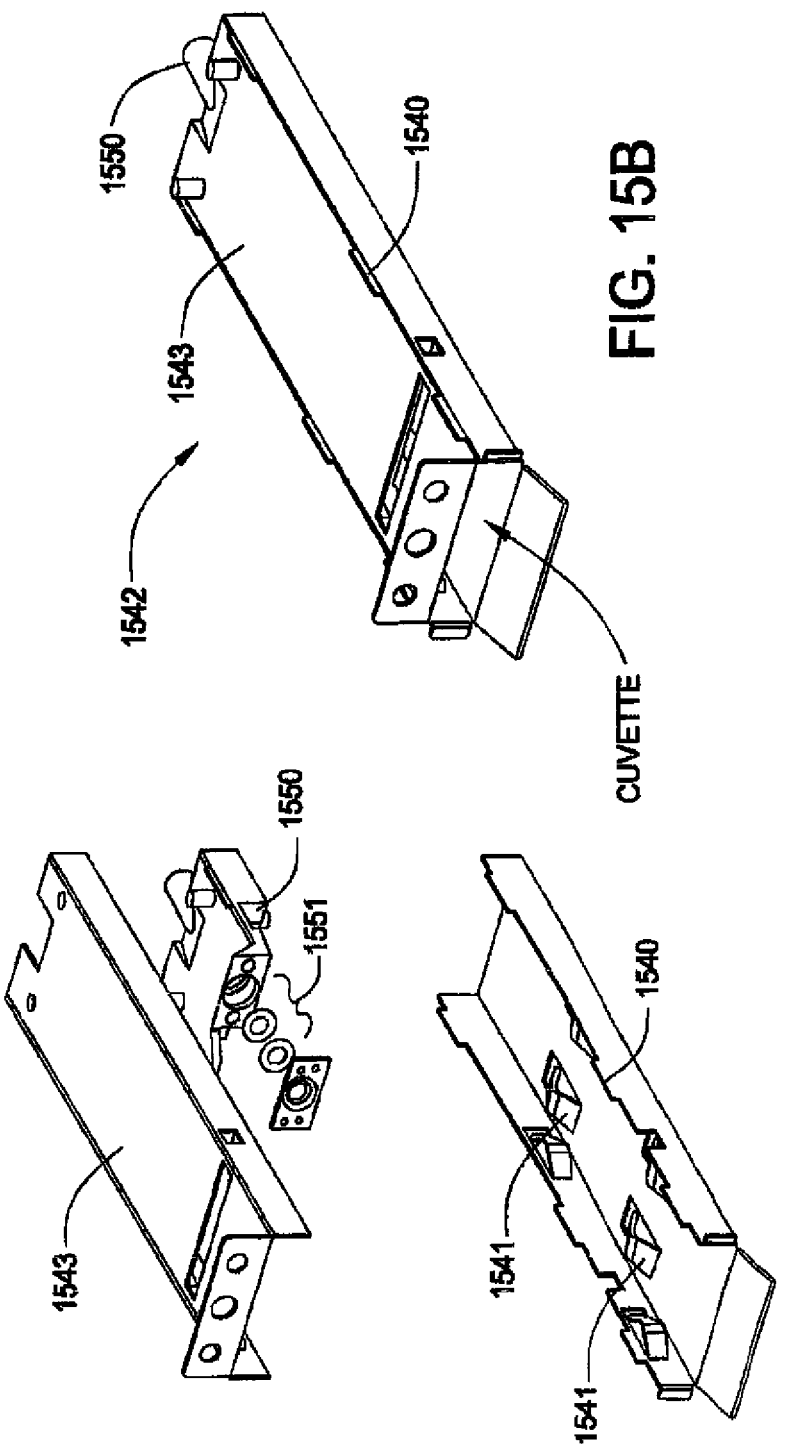

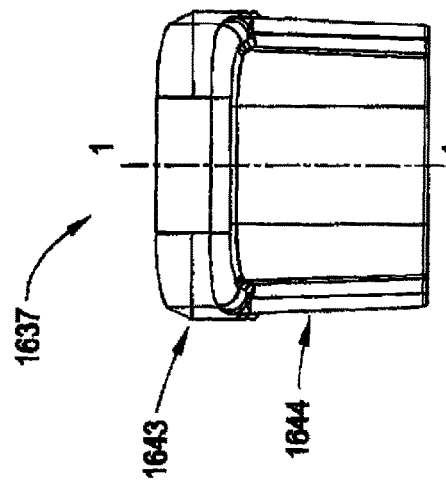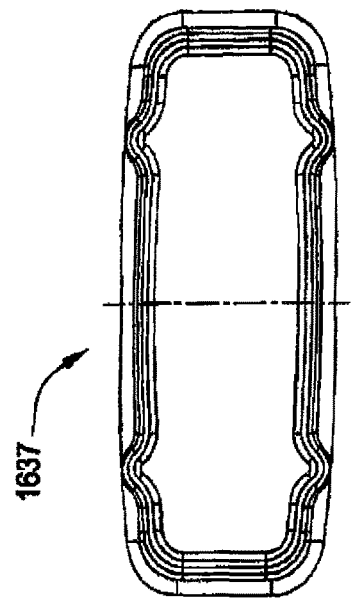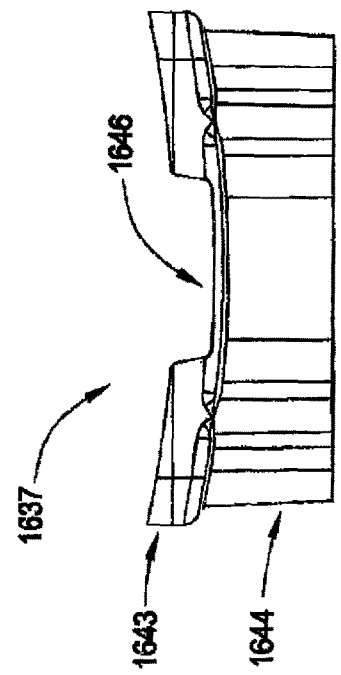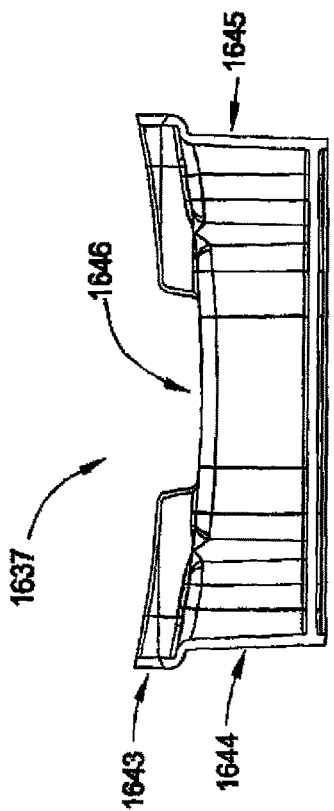

MOBILE WATER ANALYSIS

CROSS-REFERENCE TO RELATED APPLICATIONS

This application is a divisional application of U.S. patent application Ser. No. 14/874,058, entitled "MOBILE WATER ANALYSIS," filed on Oct. 2, 2015, which in turn claims the benefit of U.S. patent application Ser. No. 13/844,153, entitled "MOBILE WATER ANALYSIS," filed on Mar. 15, 2013, which in turn claims the benefit of the following U.S. Provisional Patent Applications: Ser. No. 61/658,753, filed on Jun. 12, 2012, entitled "WATER ANALYSIS DEVICES"; Ser. No. 61/710,259, filed on Oct. 5, 2012, entitled "DISPOSABLE TEST CUVETTES"; Ser. No. 61/710,294, filed on Oct. 5, 2012, entitled "CUVETTE AND SAMPLE CUP"; Ser. No. 61/710,282, filed on Oct. 5, 2012, entitled "READER AND ENCODED CUVETTE"; and Ser. No. 61/723,174, filed on Nov. 6, 2012, entitled "DETERMINATION OF SAMPLE FLUID LOCATION WITHIN TEST CUVETTES", each prior application is incorporated by reference in its entirety herein.

BACKGROUND

Accurate chemical analysis of fluids is important to many industries. For example, a high alkalinity in drinking water may result in an objectionable taste. Alkalinity is a required reporting parameter for many regulatory agencies such as the Environmental Protection Agency (EPA) and the Food and Drug Administration (FDA). The EPA has listed pH as a secondary drinking water regulation, limiting pH to 6.5-8.5. Alkalinity concentration is also a monitored parameter in regulation of industrial water discharge.

BRIEF SUMMARY

Analysis of water is commonly done using chemical reactions. In order to facilitate in-field chemical analyses, smaller mobile and hand-held analysis units have been developed. In this regard, cuvette or chip (the terms are used interchangeably herein) components are used wherein reagents are stored in a fluid channel within the cuvette such that a fluid sample, such as water, may be reacted with various chemical reagents for analysis by an associated instrument.

In summary, an embodiment provides a method, comprising: operating a motor to position sample fluid within a fluid channel of a cuvette; transmitting light through an optical chamber of the cuvette; measuring a value of received light that has been transmitted through the optical chamber; comparing the measured value of light to one or more thresholds; determining a position of the sample fluid within the fluid channel based on a comparison from the comparing step; and generating a response based upon the position of the sample fluid with the fluid channel.

Another embodiment provides a portable instrument, comprising: a housing for receiving at least one cuvette, wherein each cuvette comprises a fluid channel therein; a pump capable of creating a differential pressure in the fluid channel of the at least one cuvette to move a sample fluid into and/or through the fluid channel of the at least one cuvette; one or more processors; and a program storage device storing program code executable by the one or more processors, said program code comprising: program code configured to operate the pump and position a sample fluid within the fluid channel of a cuvette; program code configured to transmit light through an optical chamber; program code configured to measure received light that has been transmitted through the optical chamber; program code configured to compare the light measured to one or more thresholds; and program code configured to determine a leading and or a trailing edge of the sample fluid within the fluid channel based on a comparison of the light measured and one or more thresholds.

A further embodiment provides a program product, comprising: a program storage device storing program code executable by one or more processors, said program code comprising: program code configured to operate a motor to position sample fluid within a fluid channel of a cuvette; program code configured to transmit light through an optical chamber; program code configured to measure received light that has been transmitted through the optical chamber; program code configured to compare the light measured to one or more thresholds; and program code configured to determine a position of the sample fluid within the fluid channel based on a comparison of the light measured and the one or more thresholds.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 15(A-B) illustrates an example slot of an instrument.

FIG. 16(A-D) illustrates an example sample cup.

DETAILED DESCRIPTION

Figure 1:
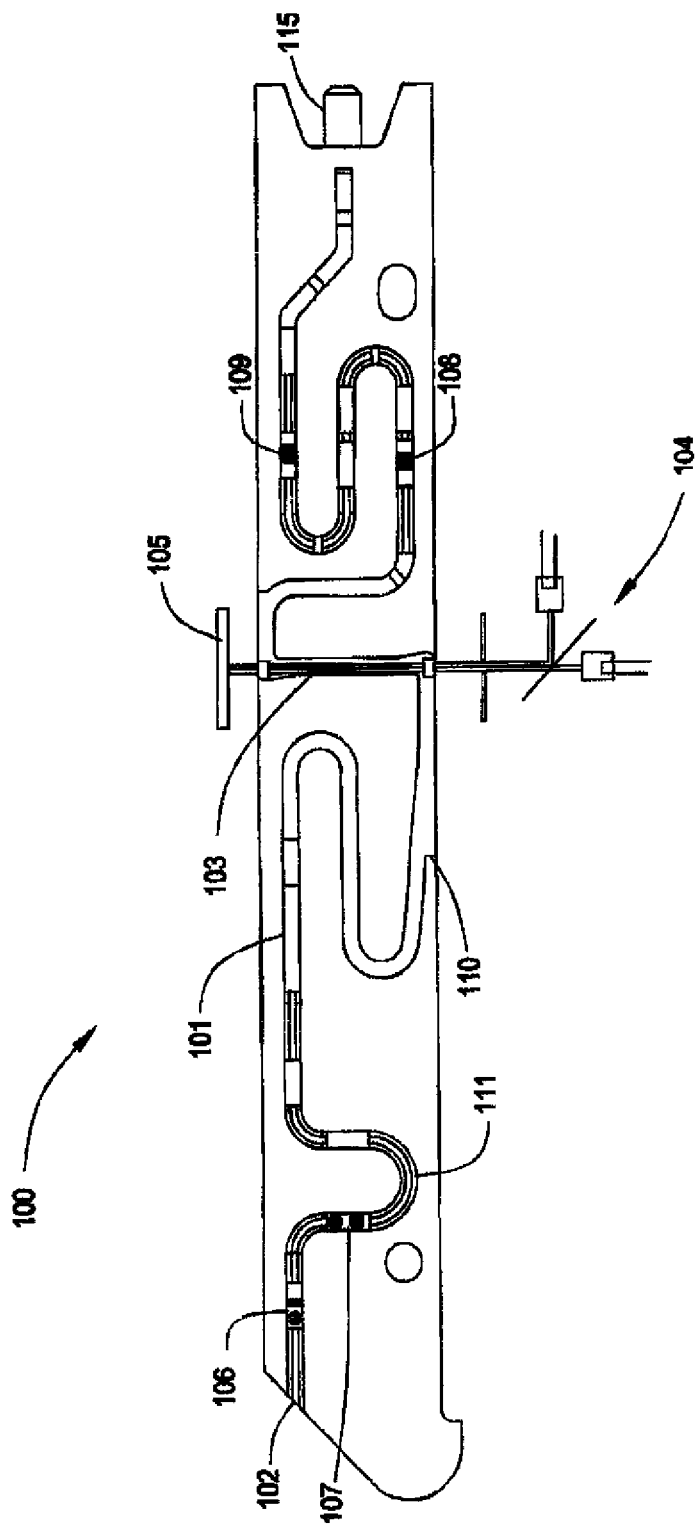
FIG. 1 illustrates a top-down view of an example cuvette with the lid removed.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Water Analysis Devices

Embodiments are directed to chip-based chemistry products and associated methods. It can be advantageous to conduct chemical analyses in the field, for example optical or colorimetry-based testing for determining chlorine content of water. Outside of a laboratory setting, a hand-held or similar mobile instrument affording accurate and precise chemical analysis is desirable, as may be used in compliance monitoring in connection with water treatment processes.

In the non-limiting example of chlorine content measurement in water, the chlorine content of a water sample may be determined via reaction with an indicator such as a dye component because the reaction produces a colored product in known proportion that in turn can be measured via a color sensitive sensor arrangement, for example, indicating a degree of light absorption of the colored product relative to a baseline, reference solution. Total chlorine and various chlorine species (for example, chloramines) may be measured in this manner, as for example described in further detail herein.

In the laboratory, such measurements are relatively straightforward to carry out. However, in the field maintaining the necessary reagents, a lack of appropriate work space, and unfavorable working conditions often create great difficulty in making such measurements. Moreover, concerns regarding accuracy, precision, and even stability (shelf life) of mobile lab products (appropriate for in-field use) make practical implementation of measurements in the field anything but routine.

Accordingly, referring to FIG. 1, embodiments provide arrangements and associated methods for field based chemical analyses, such as measurement of chlorine content in water. Various aspects provide or utilize a chip-based arrangement for analyses. In such arrangements, a chip or cuvette component 100 contains a fluid channel 101 that may include necessary chemicals in or along the fluid channel 101. The fluid (e.g., water for testing) is moved along the fluid channel 101 from an inlet 102 and is mixed with chemicals as it is drawn through the fluid channel 101, in one or both directions. Embodiments provide a hand held instrument that moves the fluid in the fluid channel 101 in a timed way, allowing for timed mixing and sequential addition of the chemicals, along with optical measurements in an optical channel 103.

Figure 5B:
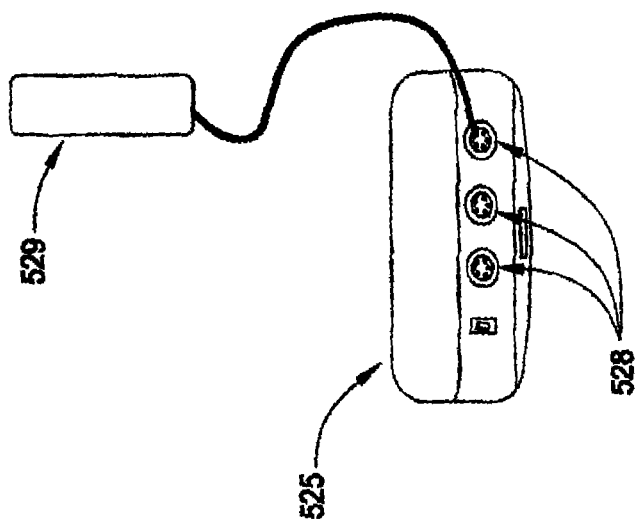
FIG. 5(A-B) illustrates an example instrument in front (5A) and top (5B) views.
Figure 5A:
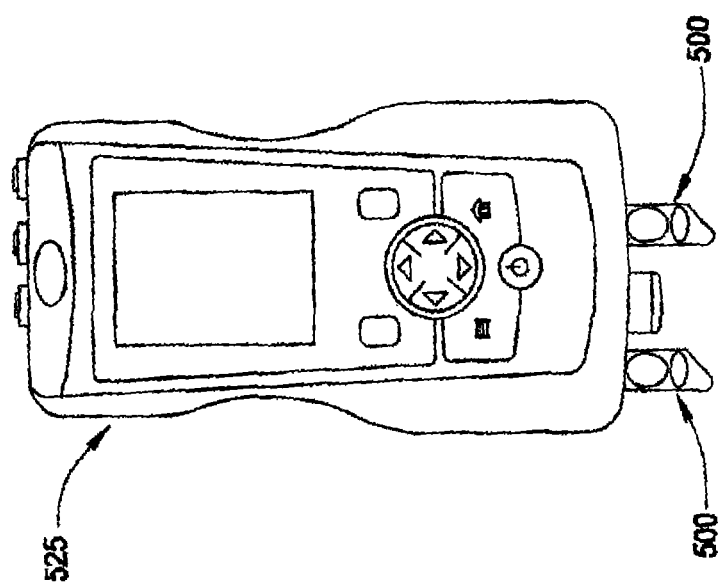

An instrument 525 (refer to FIG. 5(A-B)) draws a fluid sample, e.g., about 30 µl, into the fluid channel 101. The instrument 525 moves the fluid sample via pneumatic pressure in one or both directions within the fluid channel 101. The movement of the fluid contacts the fluid with the reagent chemicals 106, 107, 108, 109 contained in the fluid channel 101. This permits addition of reagents to the fluid in a precise fashion and timing to achieve various aims relevant to chemical analyses. An embodiment provides for first obtaining a treated fluid sample measurement (i.e., of colored fluid) in an optical channel 103 using optics 104 and a detector 105, followed by quenching of the treated fluid sample (e.g., bleaching out of color) and thereafter obtaining of a reference or blank sample measurement in the optical chamber 103.

An embodiment provides, near the sample inlet 102 to the fluid channel 101, an indicator 106 and a buffer 107. The indicator 106 may be a color generating material such as N,N-diethyl-p-phenylenediamine (DPD, forming Wurster's dye in the presence of chlorine). The indicator 106 and buffer 107 may be separately maintained, such as in adjacent areas near the sample inlet 102 of the fluid channel 101. The fluid sample thus contacts and mixes with the indicator 106 and the buffer 107 in rapid sequence. Mixing may be facilitated via controlled back and forth motion of the fluid sample within the fluid channel 101, and may occur in an area of the fluid channel 101 having one or more mixing elements (e.g., ridges, baffles, etc.). Following addition and mixing of the buffer 107 and the indicator 106, e.g., after about 30 seconds, the fluid sample is drawn into an optical chamber 103 for measurement.

Once an optical measurement is obtained, the fluid sample may be progressed further along the fluid channel 101, past the optical chamber 103, and contacted with additional chemicals. For example, the fluid sample may be contacted with a monochloramine activating agent 108 (e.g., potassium iodide, potassium bromide or other like chemicals), with additional mixing above the optical chamber 103, and then, e.g., after about 180 seconds, re-introduced into the optical chamber 103 for additional optical measurement of a colored sample.

In order to obtain a reference or blank measurement of the fluid sample, after having obtained one or more colored fluid sample measurements, an embodiment may again draw the fluid sample out of the optical chamber 103 and further up the fluid channel 101 into contact with another chemical reagent 109. The chemical reagent 109 is a blanking or quenching agent for oxidizing the colored product of earlier reactions. In the example of chlorine measurement using DPD (and thus forming Wurster's dye), for example, the chemical reagent 109 may include ascorbic acid, which oxidizes the indicator, for example Wurster's dye, such that the fluid sample may be again reintroduced, following appropriate mixing, if any, into the optical chamber 103 for a reference or blank measurement. In one example, the quenching agent is allowed to oxidize the fluid sample for approximately one (1) minute prior to obtaining the reference or blank measurement.

Thus, an example embodiment provides for drawing a fluid sample through a fluid channel 101 that contacts the fluid sample with appropriate reactants, e.g., a dye 106 and a buffer 107, provides mixing arrangements to mix the fluid sample, dye 106 and buffer 107, allows for optical measuring in an optical chamber 103, allows for neutralizing the dyed or colored fluid sample via mixing with a quenching or blanking agent 109, and allows measuring the quenched or blanked fluid sample via the optical chamber 103. Accordingly, after the dyed fluid sample is quenched, it may be re-introduced into the optical chamber 103 for reference measurement by a reverse flow action.

An embodiment allows for free chlorine measurement via drawing a measured amount of sample water into the cuvette fluid channel 101 via inlet 102 being placed within a sample of water to be tested. The water is then drawn further into the fluid channel via a pneumatic pump of an instrument 525 (refer to FIG. 5(A-B)) to contact the fluid sample with a premeasured dye 106, such as DPD. The fluid sample and dye 106 mixture is then drawn further through the fluid channel 101 to contact the dye 106 containing fluid sample mixture with predetermined amount of buffer 107. The fluid sample forms a colored product which is then drawn further into an optical chamber 103, with appropriate mixing, for measuring of color content (correlated with free chlorine concentration).

The fluid sample may be thereafter drawn further into the fluid channel 101 and past the optical chamber 103 into contact with additional chemicals or reagents. In one example, free chlorine may be measured by contacting the fluid sample with a monochloramine activating agent 108. The fluid sample may thereafter be reintroduced into the optical chamber 103 for measurement of total chlorine. The fluid sample may thereafter be quenched by drawing the fluid sample further up the fluid channel 101 and into contact with a quenching agent 109, for example ascorbic acid. The blanked or quenched fluid sample may thereafter be reintroduced into the optical chamber 103 via reverse fluid movement to obtain a blank or reference measurement.

As described herein, embodiments may provide more or fewer reagents and additional or fewer flow operations to facilitate different chemical analyses of a fluid sample.

An embodiment may be implemented with a fluid channel 101 that has a geometry substantially shaped to facilitate adequate mixing with the various chemicals included in the fluid channel 101, as appropriate for the given chemical analysis. The fluid channel 101 provides adequate retention of the fluid sample in various orientations of the cuvette 100, which allows for precise controlling of the placement and motion of the fluid sample in the fluid channel 101. This includes maintaining the integrity of the fluid sample within the fluid channel 101.

An embodiment may include a curved fluid channel 101, as for example illustrated in FIG. 1, wherein the fluid sample aliquot (i.e., amount, length) drawn into the cuvette 100 via the inlet 102 is precisely measured and is controlled to be more than the length of any straight portion of the fluid channel 101. This facilitates stability of the fluid sample position in the fluid channel 101, even if the cuvette 100 is oriented at different angles (for example, vertical, horizontal, et cetera) during use. Some example geometries are illustrated in FIG. 1.

An embodiment also includes a curved fluid channel 101 to maintain the integrity of the fluid sample without break up of the fluid sample into separate parts. In this regard, curves may be included within the fluid channel 101 to ensure the integrity of the fluid sample within the fluid channel 101. An embodiment generally provides a curved fluid channel 101 such that the fluid sample is longer than any straight portion of the fluid channel 101. In one embodiment, approximately 30 µl of fluid sample is drawn into the inlet 102 and introduced into the fluid channel 101. The curved fluid channel 101 helps to maintain the integrity of the fluid sample as it traverses the fluid channel 101, through and including traversal of the optical chamber 103, in one or both directions.

An embodiment may include a fluid channel 101 having at least one curve or jog 111 to ensure that the fluid sample maintains its integrity in the event that the chip undergoes rapid movement or a change in direction. For example, a jog 111 may be included in the lower portion of the cuvette 100 (e.g., between the dye 106 and buffer 107 positions and the optical chamber 103) in order to allow the fluid sample to maintain its integrity in the circumstance that the cuvette 100 is moved or undergoes a change in orientation. For example, if the cuvette 100 is placed in a relatively vertical position to obtain the fluid sample, yet reoriented in a horizontal position during fluid sample movement, mixing or measuring, inclusion of a jog 111 as illustrated in FIG. 1 helps to ensure the fluid sample retains its integrity and does not break into two or more parts.

An embodiment may include mixing elements along the fluid channel 101 at appropriate intervals to facilitate mixing (turbulent or non-turbulent) of the fluid sample with the chemicals or reagents disposed within the fluid channel 101. For example, an embodiment may include a mixing element formed by a restriction in the fluid channel 101 (for example, formed by reducing the fluid channel 101 cross-sectional area by about 20 percent). An embodiment may include a plurality of mixing elements as appropriate given the nature of the fluid sample and the chemical(s) disposed within the fluid channel 101. In an embodiment, mixing may be accomplished by a back and forth motion of fluid sample with respect to the mixing elements. An example geometry of the fluid channel 101 is illustrated in FIG. 1.

In an embodiment, a fluid sample drawn into the fluid channel 101 via inlet 102 is larger than the optical chamber 103 such that the fluid sample fills the optical chamber 103. This helps to ensure that the fluid sample may successfully be drawn into and past the optical chamber 103 during various movement routines.

An embodiment may include one or more specially shaped edges within the fluid channel 101, rather than sharp edges, at appropriate locations in the fluid channel 101 of the cuvette 101. The specially shaped edges help to ensure the proper movement of the fluid sample in the fluid channel 101. An example of such a specially shaped edge 110 is illustrated in FIG. 1. The fluid channel 101 may include a specially shaped or curved edge 110, for example an edge including a varying radius, at the entry and/or exit of the optical chamber 103. This facilitates the fluid sample's gradual movement along the fluid channel 101 in this region. By inclusion of such an edge 110, the fluid sample fully fills the corners in the fluid channel 101 gradually upon entry of the optical chamber 103. This reduces or eliminates the possibility of accumulation or entrapment of air in the fluid sample in this area. An example geometry of the fluid channel 101 having such an edge 110 is provided in FIG. 1.

In an embodiment, one or more curved edges are not implemented directly in the area of optical measurement, i.e., the area at which light passes through the optical chamber 103, in order to ensure an appropriate angle of light entry into the fluid sample. Therefore, an edge 110 leading to (and prior to) the optical chamber 103 is provided in the fluid channel 101, but this edge 110 does not impact light entry into the optical chamber 103. As an example, in an embodiment one or more curved edges such as edge 110 may be provided on the anterior and/or posterior entrance and/or exit of the optical chamber 103. This helps to ensure gradual entry of the fluid sample into the optical chamber 103 without impacting the angle of light entry into the fluid sample.

Chip/cuvette 100 may be made from relatively standard injection-molded thermoplastic materials such as polystyrene and polyethylene. The chemical properties of the thermoplastic must be compatible with the underlying chemistry, or interferences may occur. Applicants have found that high-grade materials are most suitable and tend to exhibit the least interfering effects. Preferred materials for the cuvette base include clear PS, and for the lid, opaque PS.

Figure 2:
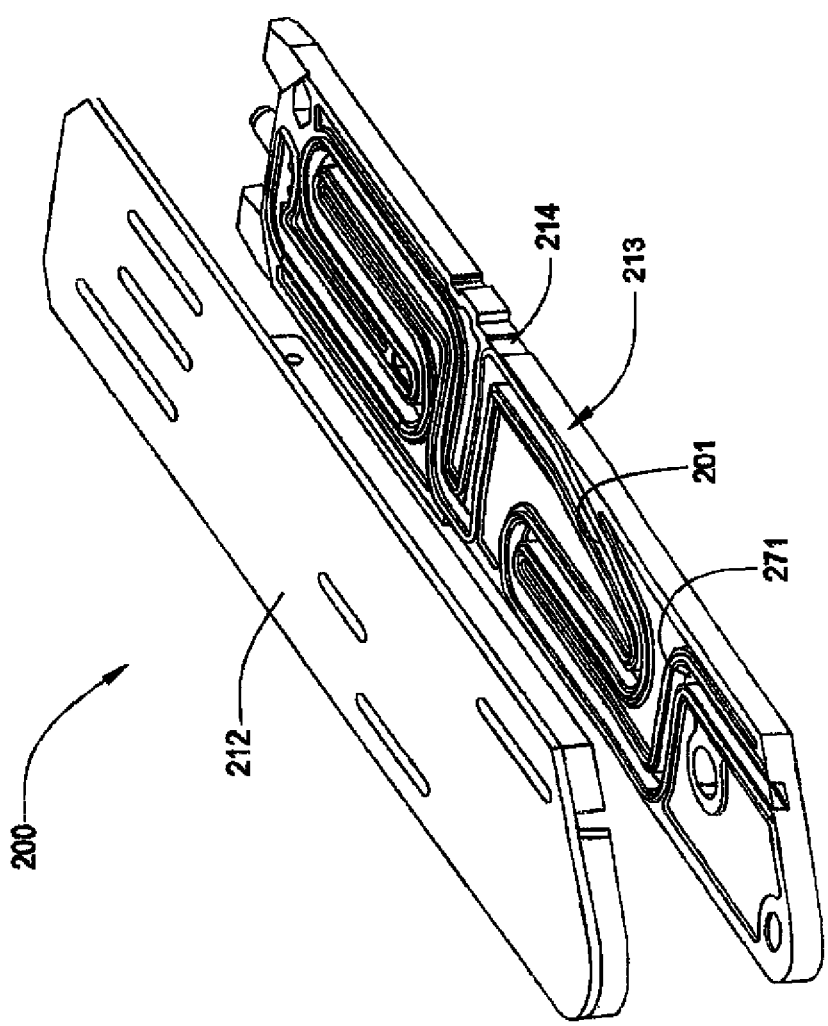
FIG. 2 illustrates an exploded view of an example cuvette body and lid.

A cuvette 100 may be modular. Referring to FIG. 2, a cuvette 200 may include a body 213 and a lid 212. During cuvette 200 assembly, since a cuvette 200 typically is not sealed until after the reagents (e.g., reagents 106, 107, 108 and 109 of FIG. 1) are disposed within the fluid channel 201, it is difficult to verify the integrity of the seal of the fluid channel 201, i.e., after assembly. If a cuvette 200 is not leak tested, there is the risk that a cuvette 200 may fail in the field. Any attempt to test for leaks after sealing in turn runs the risk of dislodging reagents within the fluid channel 201 and thereby compromising performance.

Moreover, since the cuvette body 213 may be fully open during reagent deposition, drying, and during transport up to and including where the cuvette lid 212 is affixed to the body 213, there is the risk of reagents splashing or in other ways being deposited in undesired locations in or on the cuvette 200. Moreover, the reagents may be combined with one another in an undesirable manner. It should be noted that some reagents interact catalytically, such that minute quantities in the wrong locations are sufficient to compromise performance. Drying can involve rapid changes in gas pressure or velocity that can dislodge reagents, as can vibrations or shocks/impacts during transport.

Still further, if sonic welding is used to affix the lid 212 to the cuvette body 213, there is a serious risk of dislodging/ damaging/dispersing the reagents during the sonic welding process. Sonic welding typically uses vibration frequencies of 20 kHz or more, which can easily shatter any crystalline structure into which the reagents dry. Moreover, shipping and then assembling the cuvette 200 risks damage to the windows (one of which is indicated at 214 in FIG. 2) collocated over the optical chamber 103.

In an embodiment, a cuvette lid 212 is constructed with narrow slot(s) that correspond to the location(s) where reagents are to be dispensed into the fluid channel 201. The lid 212 therefore may be affixed to the body 213 prior to dispensing the reagents into the fluid channel.

FIG. 3(A-D) illustrates enlarged views of the underside of a lid 312 having slots of various types, as further described herein. In an embodiment where a lid 312 is affixed to a body 213 of a cuvette 200 using ultrasonic welding, a ridged energy director is molded into either the lid 312 or the cuvette body 213 (e.g., as in FIG. 2 at 271) in a continuous path that surrounds the fluid channel 201 in the cuvette body 213 everywhere except the fluid inlet 102. If ultrasonic welding is utilized, reagents disposed within the fluid channel 201 may be dislodged by the energy used for ultrasonic welding. Alternatively, ridged energy director 313 may be located adjacent to the fluid channel 101 in cuvette body 213, as shown in FIG. 2.

Accordingly, an embodiment provides slots 315-318 in the lid 312 such that the lid 312 may be welded to the body 213 prior to reagent dispensing into the fluid channel 201. Thus, the welding and sealing of the lid 312 to the body 213 occurs prior to dispensing the reagents into the fluid channel 210.

Figure 3B:
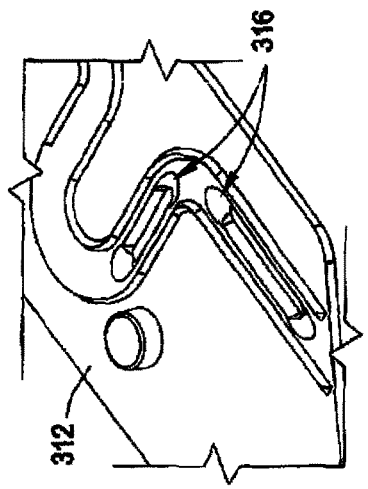
FIG. 3(A-E) illustrates enlarged views of example slots in cuvette components.
Figure 3D:
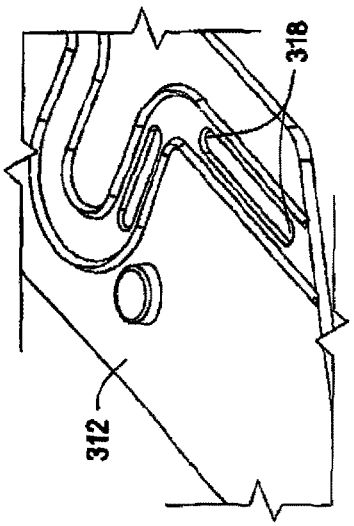
Figure 3A:
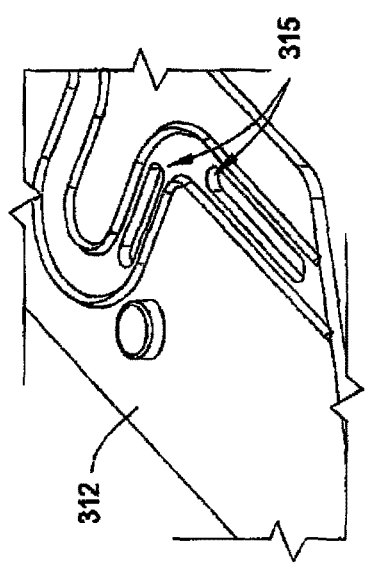

In FIG. 3A, a lid may include slots having sharp edges 315. The sharp edges 315 are essentially perpendicular to the flow of fluid within the fluid channel 201. In the event that the sharp edges 315 disturb fluid flow within the fluid channel 201 in an undesirable way, other edges may be employed.

For example, FIG. 3B illustrates an example of a slot employing a scooped edge 316. The scooped edge provides for an angled transition for fluid of the fluid channel 201 entry into the slot of the lid 312. Thus, as fluid enters the scooped edge 316 of the slot, the angled transition is smoother. This smoother transition (compared to sharp edge 315) facilitates entry of the fluid into the slot of the lid. This may be desirable, as the slot in the underside of the lid 312 will remain after cuvette 200 sealing. The cuvette lid 312 will have its top side 219 (refer to FIG. 2) covered with a lid seal. Thus, the cuvette 200 will be sealed after the lid 312 has been affixed to the cuvette body 213, e.g., via ultrasonic welding of the ridged energy director 313.

Thus, it will be appreciated by those skilled in the relevant art that if the slots in the lid 312 are formed as simple cuts in the lid such that the slots have sharp edges 315, the sharp edges 315 on the boundaries of the slots may facilitate air bubble formation in the fluid sample, which is undesirable.

Figure 3C:
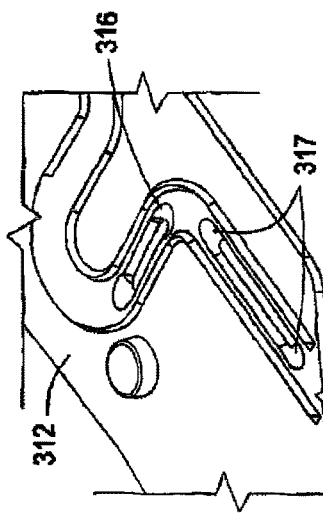

This may compromise the ability to make optical readings in the optical chamber 103. To counteract this, in some embodiments the entire slot can include angled edges, or only a portion (e.g., leading and lagging edges) may be shaped. Various angled edges may be utilized, such as the scooped edges 316 illustrated in FIG. 3B, rounded edges 317 illustrated in FIG. 3C, or beveled edges 318 illustrated in FIG. 3D. Moreover, some suitable combination of the foregoing may be utilized, as illustrated in FIG. 3C.

Figure 3E:
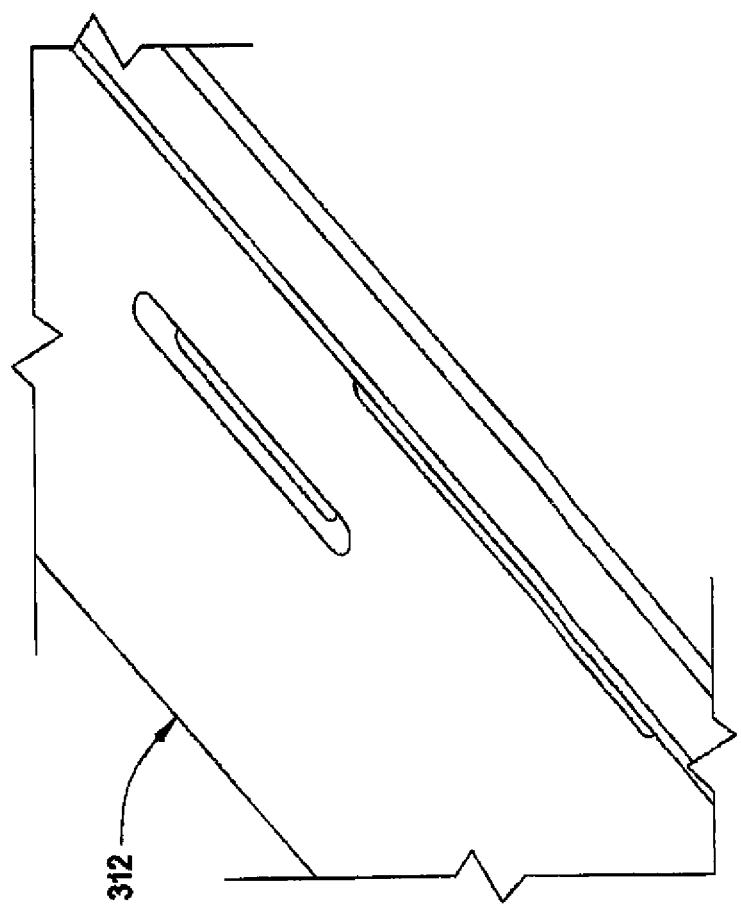

FIG. 3E is an alternate embodiment of the lid wherein the ridged energy director has been removed to the body.

Figure 4A:
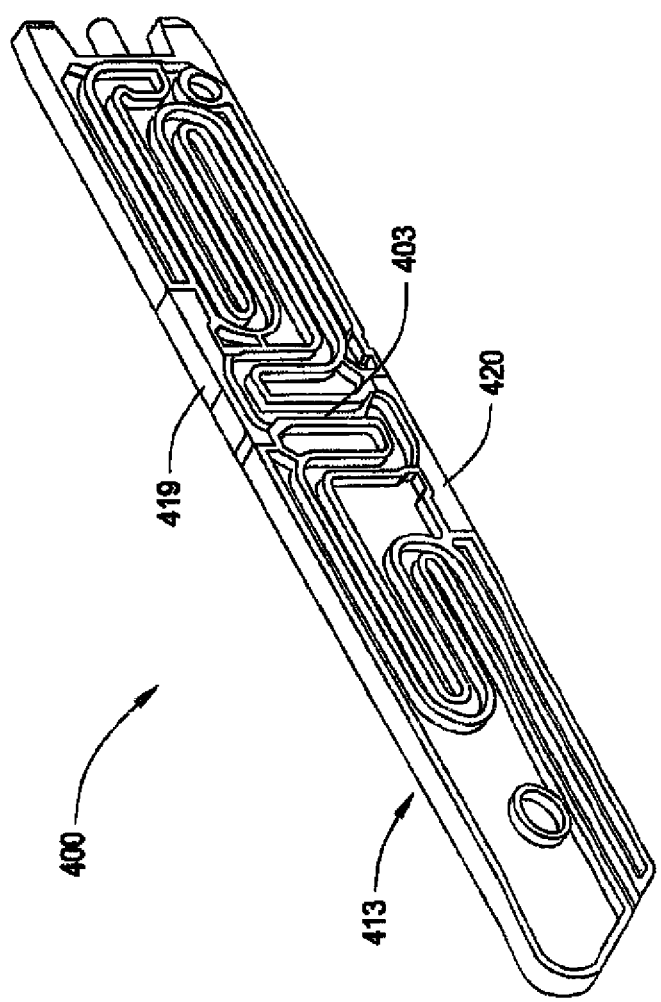
FIG. 4A is a computer-generated side view of a cuvette body.

Illustrated in FIG. 4A is a cuvette body 413 having separately molded optical windows 419, 420 bounding the optical chamber 403. Thus, the cuvette body 413 is formed via a first process (e.g., injection molding) followed by incorporate of the optical windows 419 and 420 via a second process (e.g., second injection molding). This may be necessary where the cuvette body 413 is formed of opaque material such that different material (e.g., transparent or translucent material) is utilized to form the optical windows 419, 420 in order to allow light from the optics 104 to pass through the optical chamber 403.

Figure 4B:
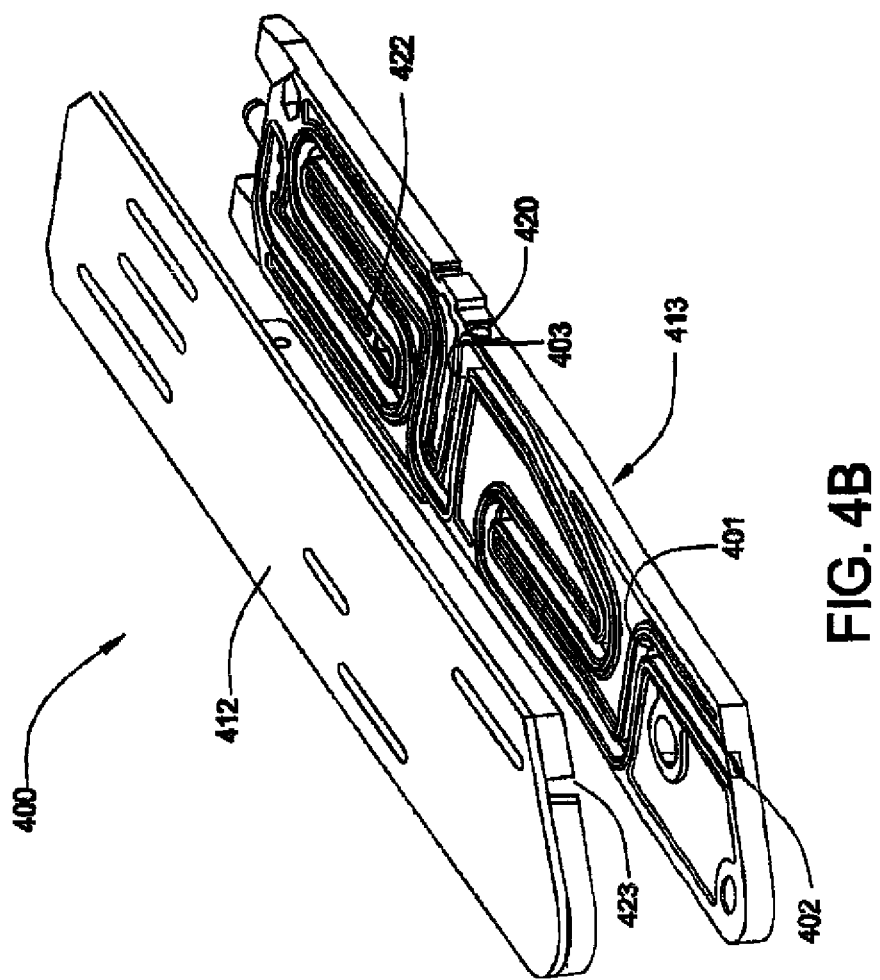
FIG. 4B is a computer-generated exploded view of an example cuvette body and lid.

As illustrated in FIG. 4B, the additional process for forming optical windows 419 and 420 may be avoided by using a single process wherein the cuvette body 413 is molded from material suitable for the optical windows (e.g., transparent or translucent material). Therefore, rather than incorporating separately formed optical windows 419, 420, as illustrated in FIG. 4A, in an alternative embodiment, the cuvette body 413 is molded of a material that allows light from optics 104 to pass there-through. Thus, optical window areas (one of which is illustrated in FIG. 4B at 420) may be formed within the material of the cuvette body 413, eliminating a need for additional processing step(s) (e.g., additional injection molding). The optical window areas, e.g., area 420, may be located in a similar location to that of windows 419, 420 of FIG. 4B.

The optical windows 419, 420 or the optical window area 412 may be formed in the cuvette body 413 as highly polished and curved structures. This creates optical lenses collocated with the optical chamber 403. In the embodiment of FIG. 4B, the lid 412 may be constructed separately of opaque material and include apertures 422, 423. Aperture 423 permits fluid sample inlet to the inlet 402 of the fluid channel 401 and aperture 422 permits light passage through opaque lid material of the lid 412 for optical analyses to be conducted via the optical chamber 403.

Since the cuvette body 413 may be molded entirely of light transmitting or translucent material, it may be beneficial to substantially enclose the body with an opaque material, e.g., via providing a lid 412 or other covering of opaque material, in order to prevent or reduce ambient light or overfill light from optics 104 from entering the cuvette 400. In the example of FIG. 4B, the lid 412 prevents light from entering through the clear transparent or translucent body 413, except where the lid 412 contains apertures 422, 423. Additional covering material may be provided.

Reader and Encoded Cuvettes

Referring to FIG. 5(A-B), embodiments provide a hand held instrument 525 for field-based chemical analyses, such as measurement of chlorine content in water. In a lab-on-a-chip system, the cuvette 500 is inserted into a slot of the instrument 525. Once inserted, the cuvette 500 is dipped into fluid sample (refer to FIG. 11) and the fluid sample is drawn into the cuvette 500 for reaction with one or more reagents disposed therein for analysis. The cuvette 500 contains a fluid channel 101 (refer to FIG. 1), internal thereto that may include necessary chemicals in or along the fluid channel for fluid sample analyses. Accordingly, the cuvette 500 and fluid channel 101 thereof provide for mixing and transport of the appropriate chemicals for the analysis of a fluid sample as it is drawn through the fluid channel, in one or both directions, by the instrument 525.

In an embodiment, the instrument 525 comprises communication ports 528, as illustrated in FIG. 5B. The communication ports 528 may be used for example for plugging in additional component(s) 529 for use with the instrument 525. For example, the instrument 525 may be used in combination with a pH probe or a dissolved oxygen probe as an additional component 529 via connection with a communication port 528 of the instrument 525. Accordingly, the instrument 525 may provide both on-chip analyses of fluid sample via cuvettes 500 and/or other analyte analyses, for example via use of additional component(s) 528, for example pH or dissolved oxygen metering. The instrument 525 may therefore include complimentary functionality such as for example provided by a pH and/or dissolved oxygen electrochemical probe. An example of such functionality for pH and/or dissolved oxygen metering is included in the Hach HQ40d Portable pH, conductivity, dissolved oxygen, ORP, and ISE multi-parameter meter, available from Hach Company of Loveland, Colo. The instrument 525 thus may incorporate communication ports 528 and functionality supporting metering using inputs from various additional probes of components 539. Examples of additional probes or components 529 that may be connected to the instrument 529 include but are not limited to IntelliCAL PHC101 Standard Gel Filled pH Electrode, IntelliCAL LDO101 Rugged Luminescent Dissolved Oxygen (LDO) Probe, and/or the IntelliCAL PHC301 Standard Refillable pH Electrode, available from Hach Company of Loveland, Colo. Moreover, the instrument 525 may include a power port (for charging of a battery of the instrument 525) as one of the ports 528, which may be a dedicated power port or a combination power/data port.

The instrument 525 slot, into which a cuvette 500 is inserted, may include a tray that houses the cuvette 500 in a releasable fashion. The tray may be equipped with an element for regulating the temperature of a cuvette 500. For example, a tray may include a heating element disposed therein to facilitate heating of a cuvette 500 inserted into a slot of the instrument 525. The element, such as a heating element, may be powered using battery power supplied by the instrument 525. A heating element may be used in a tray for example to increase the overall temperature of the cuvette 500, such as when outdoor and/or environmental conditions warrant, for example to provide adequate temperature regulation for a chemical reaction within the cuvette 500 during fluid sample analysis.

Various analyses may be conducted using the cuvettes 500, depending for example on which type of cuvette 500 (chemical reagents placed along the fluid channel thereof) and/or which analysis routine are chosen (e.g., how the fluid sample is moved through the fluid channel by the instrument 525, the timing and order of optical measurements taken by the instrument 525, etc.). Accordingly, as different cuvettes 500 may be used with the instrument 525 for various analyses, an embodiment provides an encoded cuvette for reading by a reader component, for example provided by (within) the instrument 525.

Figure 6:
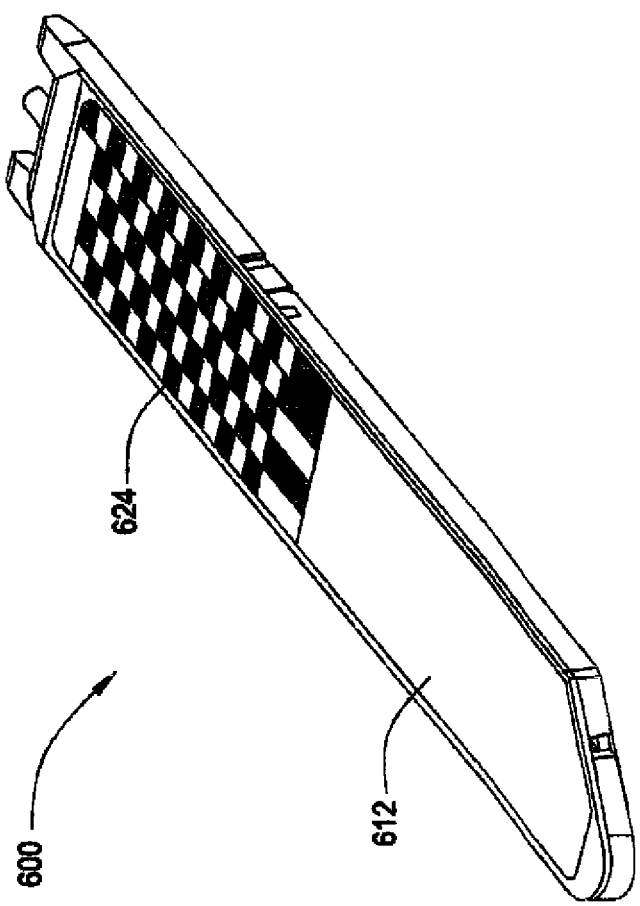
FIG. 6 illustrates an example cuvette having an encoded area.

Referring to FIGS. 6 and 7(A-B), an encoded cuvette 600 may contain an encoded area 624 that is encoded with information that is readable or otherwise interpretable by another component of the system, such as a reader 730. The encoded area 624 may convey information including but not limited to information for identifying the type of cuvette 600 with respect to its chemistry or information conveying which fluid sample movement routine should be executed by the instrument 525 in connection with the cuvette 600.

Figure 7A:
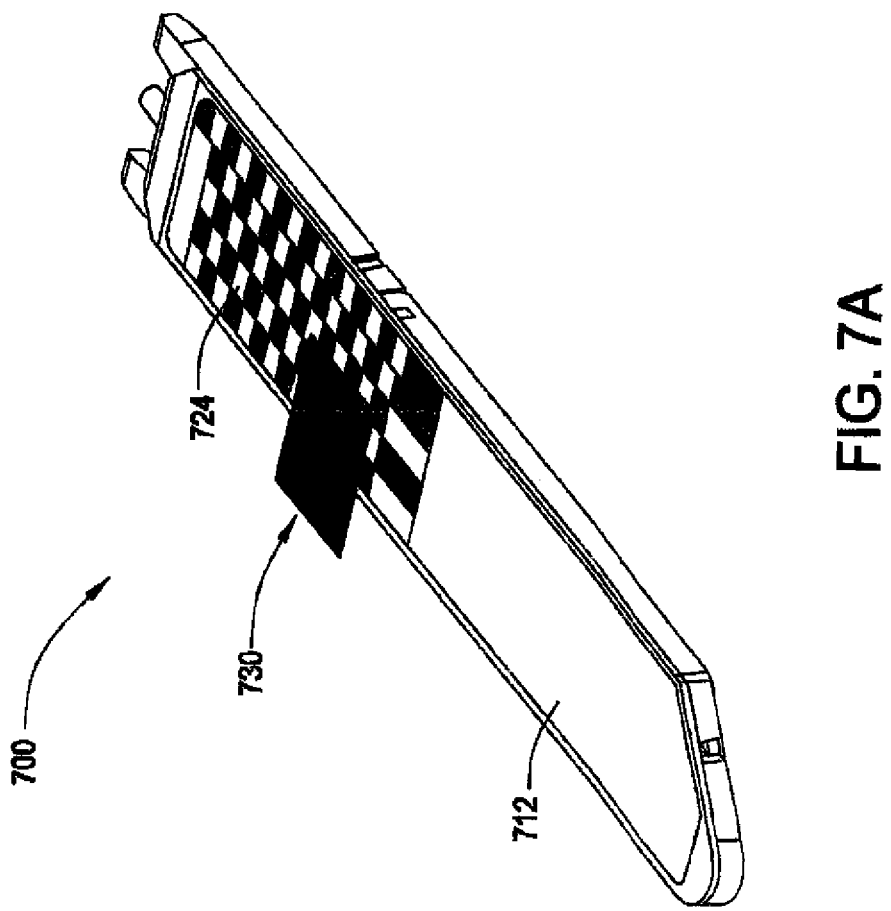
FIG. 7A illustrates an example cuvette and reader.

For example, referring to FIG. 7A, a cuvette 700 may have a pattern printed thereon in the encoded area 724 in order to impart to a reader 730 information relevant to the cuvette 700. In addition to a printed pattern (for example, an optically read pattern), the encoded area 724 may utilize other techniques, such as for example magnetically encoded information or radio frequency identification (RFID) tag/reader combinations. Example information encoding arrangements and/or patterns are further described and illustrated herein.

In an example embodiment, multiple slots of the instrument 525 may be provided for insertion of cuvettes 500. Each of the slots of the instrument 525 may likewise include a reader 730 that reads the encoded area 724 of the cuvette 700. For example, a reader 730 may be disposed within a slot of the instrument 525 such that when the cuvette 700 is inserted into the slot of the instrument 525, the encoded area 724 is disposed towards the reader 730 and thus readable.

Different cuvettes 700 may be used in the different slots of the instrument 525 simultaneously and may be distinguished by the reader 730 by virtue of inclusion of the encoded area 724 on the cuvettes 700 inserted into the instrument 525. Thus, multiple samples and multiple measurement types and/or routines may be made by the instrument 525 in parallel or substantially in parallel. An embodiment therefore permits multiple chemical analyses of a similar (or dissimilar) type to be run in parallel. By virtue of the encoded area 724 information, the instrument 525 of the analysis system may ascertain which cuvettes 700 have been inserted into the slots of the instrument 525, and may execute the appropriate analysis routines. The reader 730 thus communicates the information read from the encoded area 724 to the instrument 525.

In an embodiment, each slot of the multiple slots may be configured to read the cuvette 700 type inserted and execute an appropriate routine. For example, one cuvette 700 of type A may be inserted into the instrument 525, which has a reader 730 disposed within a slot of the instrument 525 and positioned to read the encoded area 724, and configure a sub-component (memory, processor, pump units and the like) to execute a first routine. Another cuvette 700 of type B may be inserted into the instrument 525 and likewise be read, triggering a sub-component to execute a second routine. Thus, cuvettes 700 of type A and type B may be inserted to run different chemical analyses on a sample in parallel and/or simultaneously (free chlorine, total chlorine, monochloramine, alkalinity, magnesium, et cetera). In one embodiment, four different slots are made available in the instrument 525.

The cuvettes 700 of different types may be read as they are inserted, for example via provisioning of a reader 730 proximate to a slot of the instrument 525 that contains an optical (bar code type) reader functionality. Such a reader 730 may read an imprinted pattern on the cuvette's encoded area 724 as it is slid into a given slot of the instrument 525.

The reader 730 provides for a low cost way to read data encoded within the encoded area 724 of the cuvette 700. In one embodiment, the reader 730 reads data in the form of rectangles printed onto a very low cost label applied to a cuvette 700. The encoded area 724, and rectangles printed thereon, thus move past the reader 730 as the cuvette 700 is inserted into the slot of the instrument 525 as the surface of the cuvette 700 having the encoded area 724 is passed under the surface of the reader 730. The physical volume available to accomplish this may be very limited in mobile or hand held instruments 525, precluding previous reader designs. The reader 730 is configured to reliably function even when the velocity of the encoded area 724 label changes in an erratic manner.

Accordingly, while many other optical readers, such as bar-code readers, require a relatively large distance in order to function properly, on the order of inches, in the direction normal to the plane of the label being read, an embodiment provides a reader 730 that is capable of reading a label of the encoded area 724 that is much closer, on the order of millimeters.

Other, conventional optical readers only read a single track at a time, containing both clocking and data information. To facilitate clock recovery, this necessitates that the scanning be made at a relatively consistent speed. In contrast, an embodiment may read multiple tracks at a time and accommodates speed variations when reading a label of the encoded area 724, such as often occurs with cuvette 700 insertion into a slot of the instrument 525.

Figure 7B:
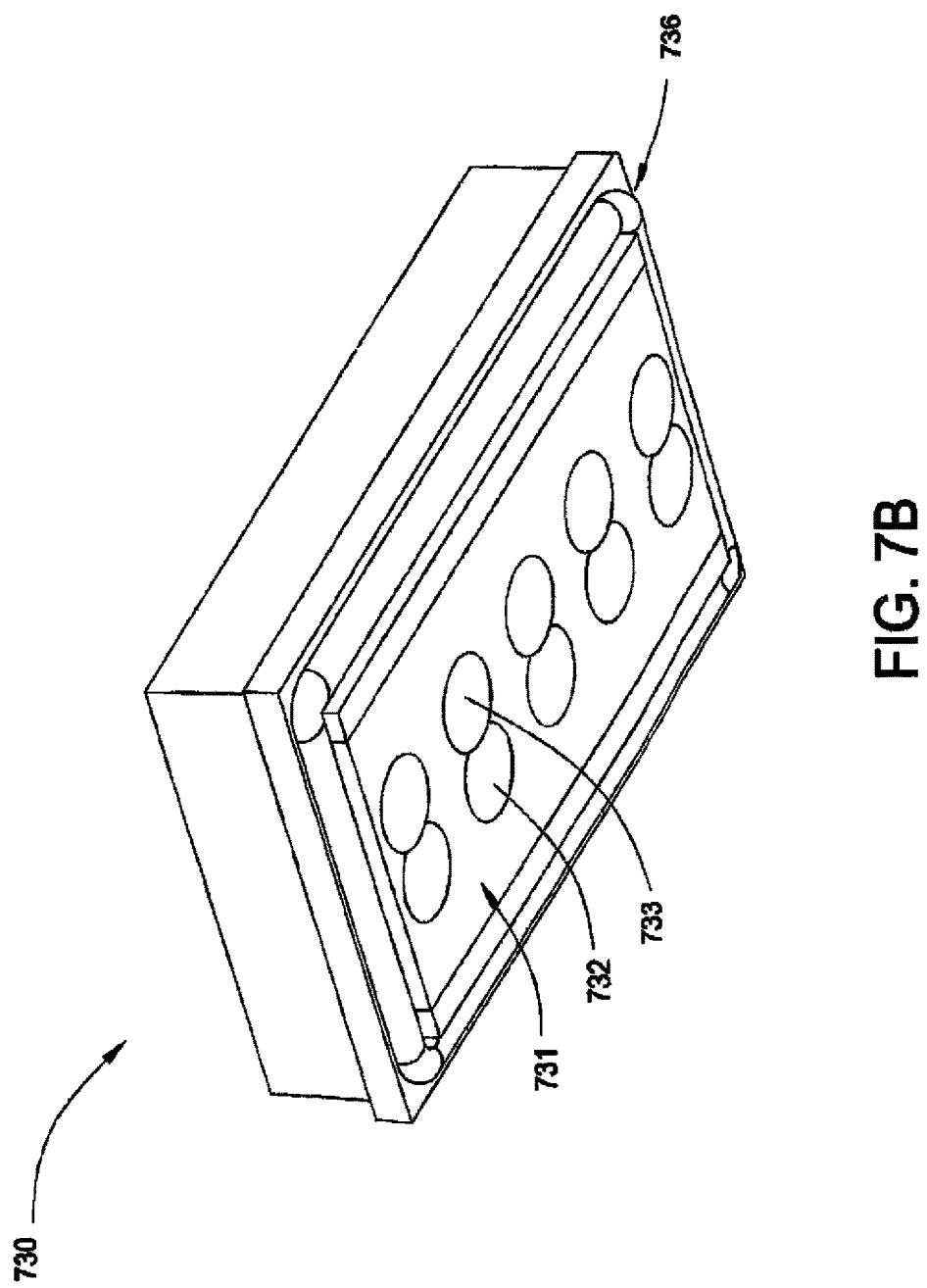
FIG. 7B-C is a close-up view of the reader.

Referring to FIG. 7(A-B), an embodiment provides a reader 730 having a light source. The light source illuminates the encoded area 724 and reads reflected information. In a particular, non-limiting example embodiment, referring to FIG. 7B, infrared (IR) light is emitted from an array 731 having five light emitting diodes (LEDs) and focused on an optical element comprising five lenses, one of which is indicated at 732. This illuminates a region of the label of the encoded area 724 to be read. The light reflecting from a smaller detection region of the label of the encoded area 724, of for example approximately 0.7 inches, is focused by a similar optical element comprising five lenses, one of which is indicated at 733, onto five IR light detector transistors (photodetectors) of the reader 730.

For example, more light may be reflected from areas of the encoded area 724 label representing logical ones than from areas of the encoded label 724 representing logical zeros. The detector transistors allow an electrical current to pass through which is proportional to the amount of light detected (falling on it). As the label of the encoded area 724 passes under the reader 730, the detection region effectively moves along the axis of the label of the encoded area 724, producing a time varying voltage proportional to the IR reflectance of the label surface. This voltage, along with the voltage from four other identical photodetectors (in a five photodetector array 731) is filtered and sampled by an analog to digital converter, and processed by a microcontroller to produce digital data bits used to encode information about the cuvette 700 to which the label is attached (encoded area 724). Cuvette may include an area 1042 for grasping the cuvette (non-encoded). Error checking bits may be included in the encoded data of the encoded area 724 to facilitate integrity verification.

An embodiment differs significantly from conventional optical readers in a variety of ways. For example, unlike other optical readers, which require inches of space between the reader and the label to be read, an embodiment operates using only a few hundredths of an inch between the encoded area 724 label and the reader 730. The reader 730 itself is unusually small, being only a few tenths of an inch high.

Figure 7C:
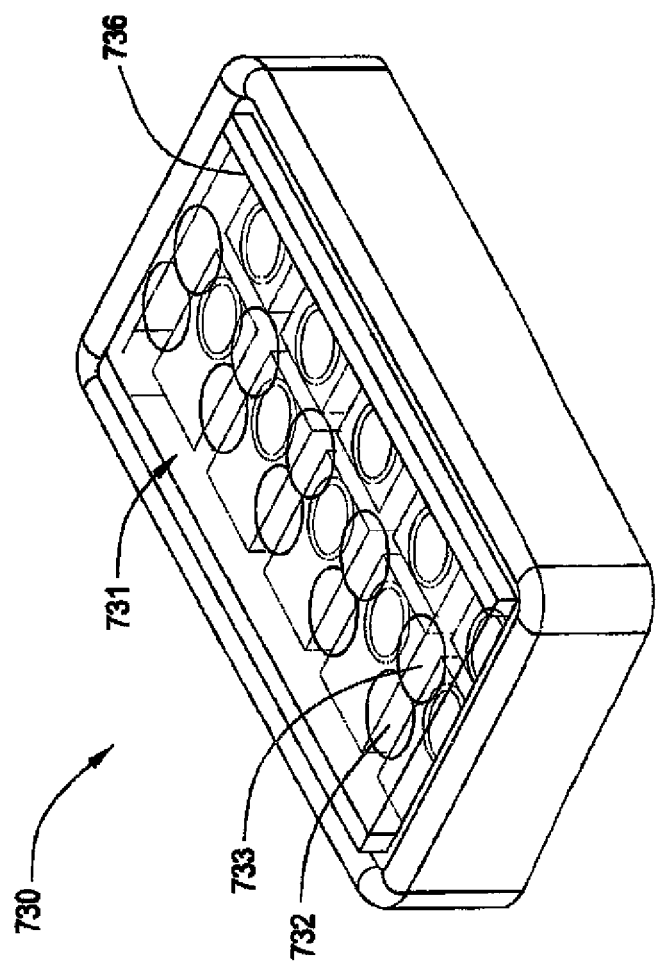

For example, in FIG. 7C the distance from the top of lens 732/733 to the surface of the cuvette barcode label 724 is approximately 0.06 inches.

Additionally, the reader 730 accurately reads data from encoded area 724 labels printed in a low resolution, low quality manner. The reader 730 may also have no moving parts. The reader 730 may incorporate a single optical array 731, that may be fabricated of clear optical quality plastic and which performs the function of ten independent components (in the example illustrated in the FIG. 7B).

Figure 8:
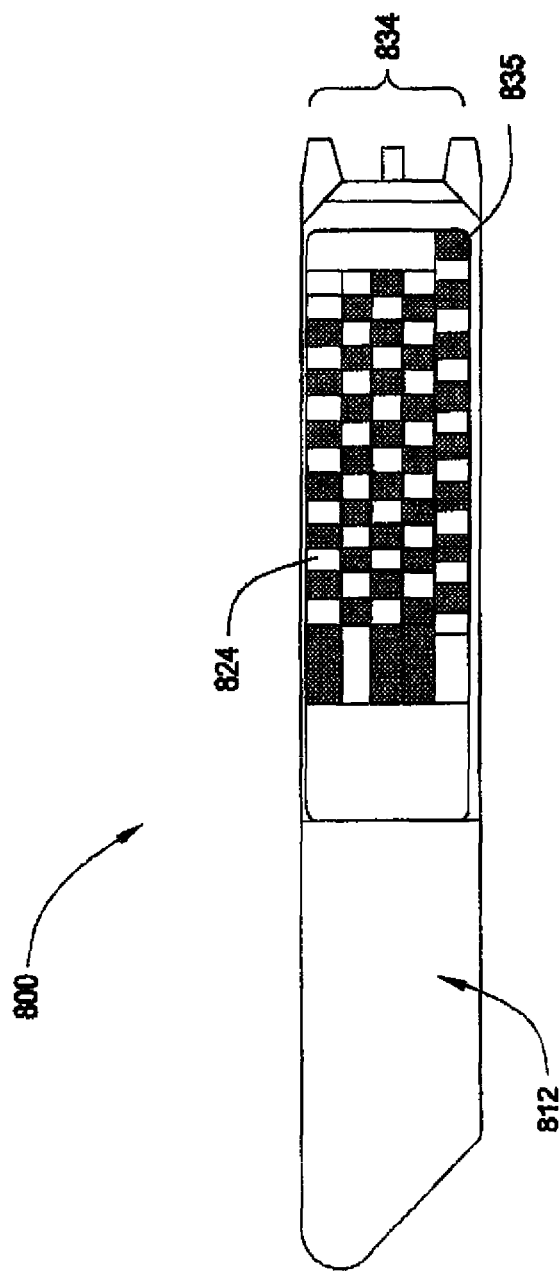
FIG. 8 illustrates an example cuvette having an encoded area.

With attention directed to FIG. 8, the data encoding format of the encoded area 824 in one example includes multiple "data" tracks 834 (e.g., including information on chemistry of the cuvette 800) and a single clocking track 835. The clocking track 835 may be skewed (for example by half a bit period) such that a transition on the clock track 835 indicates the center of a bit on each of the data tracks 834. Incorporating a clocking track 834 in this manner allows for data to be properly decoded regardless of the speed of insertion of the cuvette 800 into a slot of the instrument 525. It is even possible to pause the insertion of a cuvette 800 for an arbitrary period of time during the insertion process.

Thus, an embodiment allows for a physically compact, low cost method of reading encoded areas, e.g., 824 used to identify the cuvettes 700, 800, for example on insertion into the instrument 525. Other arrangements for encoding and reading cuvette information are of course possible, as further described herein. Use of a printed pattern within the encoded area 824 may preclude the need for additional lasers and mirrors in a reader 730, which may in turn reduce the overall size of the system. In response to reading the cuvette encoded area 824, the instrument 525 may be automatically configured to run the appropriate routine for the identified cuvette type.

When formed together, as shown in the collapsed view of FIG. 7A, the cuvette's 700 encoded area 724 is disposed on (or integrated into) the cover 712 in a position that, when it is inserted to a slot of the instrument 525, the pattern information is read by a reading component 730 of the instrument 525.

In the non-limiting example of FIG. 7B, which illustrates the underside of a reader 730, an array 731 of ten lenses communicates emitted and reflected light between five emitting diodes and five photodetectors. Each pair of lenses communicates radiation between diodes and photodetectors and reads one of the "columns" or tracks (e.g., 834, 835) comprising the pattern of the encoded area 724 as the cuvette 700 is slid into the instrument 525 (and thus past the reader 730). The emitting diodes and photodetectors may be mounted on a circuit board (not shown for clarity). Between the emitting diodes/detector is an array 731 that includes lenses or other optics and a light shield 736 may also be provided, as illustrated in FIG. 7B. There may be one lens 732 for each emitting diodes and one lens 733 for each photodetector (for a total of ten). The array 731 focuses the emission from the emitting diodes onto the encoded area 724, then the photodetector lenses 733 focus reflected light from the encoded area 724 onto the photodetectors. FIG. 7A illustrates an example reader 730 in relation to a cuvette 700. As illustrated, in one example embodiment, the array 731 lenses of the reader 730 are only about 4 mm from the encoded area 724.

FIG. 7B illustrates the underside of the reader 730 (i.e., the side that faces the cuvette 700). The lens array 731 may be made of a material that transmits the emitting diodes' emission (for example, polycarbonate, acrylic, polystyrene, or glass). The light shield 736 may be a black santoprene rubber-like material or other suitable material for shielding out ambient light.

Figure 9:
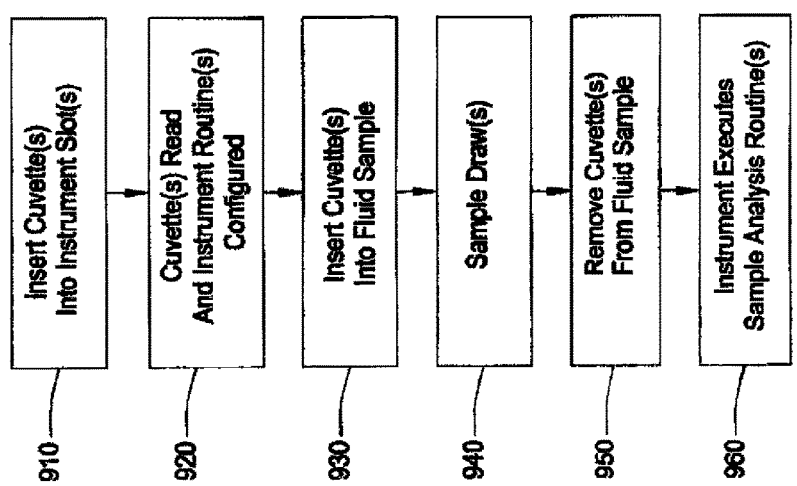
FIG. 9 illustrates an example method of analyzing a fluid sample using a mobile water analysis instrument.

In an example method, referring to FIG. 9, a user in the field may desire to run tests on water to determine chlorine concentration. The user may insert an encoded cuvette into a slot of the instrument 100 at 910. The reader 730 reads the cuvette's encoded information at 920, for example information as printed on a label and placed in encoded area 724. The instrument 525 therefore may be automatically configured to run an appropriate routine matching the cuvette's chemistry. Alternatively, the user may manually select a routine via interfacing with a user interface provided by the instrument 525.

The user may then place the encoded cuvette into the fluid sample at 930, for example dip the cuvette tips or end portions into the fluid sample. In an embodiment, the instrument 525 may include a sample detect feature (refer to FIG. 11) to determine the cuvette tips are appropriately located in the fluid sample, e.g., via an electrical circuit being formed via electrical connection of fluid sample sensitive (contact) electrodes being in electrical connection via a conductive fluid sample. At 940, after ascertaining the cuvette is properly positioned within the fluid sample, the instrument 525 may signal as much to the user, for example via light, sound (e.g., speaker, beeper) or otherwise, and begin to draw fluid sample into the cuvette, e.g., via inlet 102.

Once a sample has been drawn into the cuvette, the user then removes the cuvette tip from the fluid sample at 950. The instrument 525 may again confirm this via a fluid sample detection feature. Thereafter, at 960, the instrument 525 may then initiate the appropriate predetermined routine of fluid sample movement within the fluid channel 101 for the given cuvette's chemistry, as ascertained via user input, cuvette encoded information area 724, or otherwise.

Obtaining samples in parallel may follow a similar routine as that described above. Obtaining samples in parallel may again include obtaining samples for different chemical reactions/analyses using different cuvettes, having either the same or different predetermined routines and chemical reagents, as appropriate for the desired chemical analyses and as determined from the cuvettes' encoded areas 724.

Some non-limiting example implementations of cuvette encoding areas 724 are now described. Although specific example encoded areas 724 are described herein, other encoded areas may be utilized.

Figure 10:
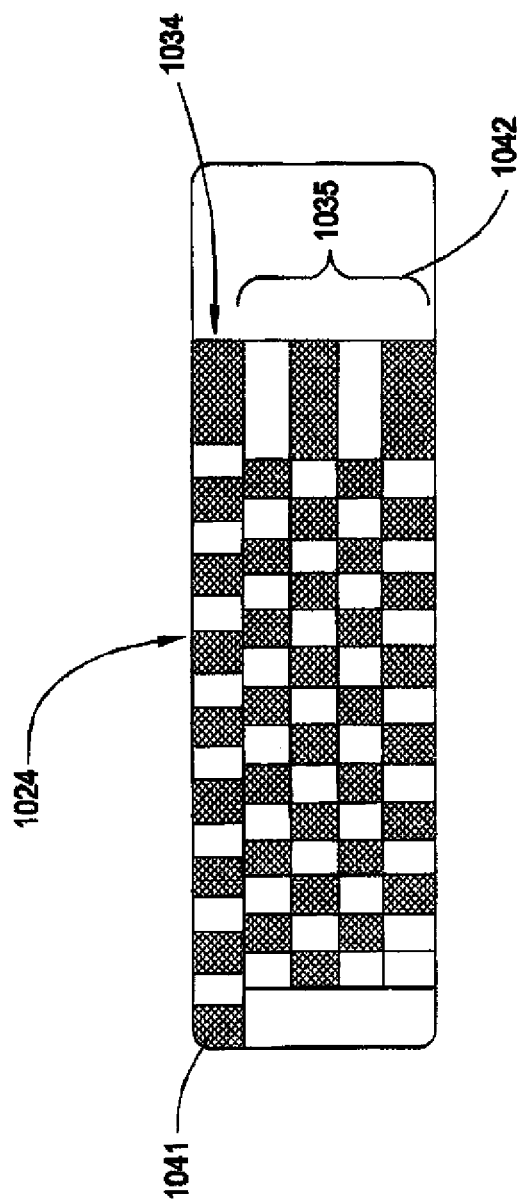
FIG. 10 illustrates an example of an encoded area of a cuvette.

FIG. 10 provides a specific, non-limiting example of a pattern label for use in an encoding area 1024. In the example, a bit corresponds to a pattern area (a dark or light rectangle in the illustrated examples). In one example label, a maximum of 32 chemistries are available via different patterns encoded in the label, although other chemistries may be available. For example, to have room for 64 different encoded label chemistries, then one more bit may be used. The encoded area 1024 may include a lot/date code, a position (lot position) code, chemistry type code, slope correction code for particular chemistries and/or cuvettes, routine code, lot expiration dates, and the like. A checksum may also be included for verification of the encoded data. For example, 8 bits may be used for verification.

In an example, the encoded information of the encoded area 1024 may be encoded in 46 bits broken down as follows: 6 bits for chemistry identification (64 potential chemistries); 7 bits for the date (year); 9 bits for the date (day); 16 bits for the lot code; and 8 bits for checksum. Such an encoding arrangement assumes the routine/fluid handling method does not change based on the lot. Another example is 26 bits: 6 bits for chemistry identification (64 potential chemistries); 12 bit charge number; and 8 bits for checksum.

Another example encoded area 1020 may use 40 bits, with 4 bits used for the version code, 1 bit used to indicate whether a previous version is usable (e.g., if the current version is not supported by the instrument 525), 15 bits for date (e.g., days from a particular date), 8 bits for slope adjustment (e.g., supporting slope adjustments for the various cuvette chemistries), 6 bits used for offset adjustment for particular cuvette chemistries, and 6 additional bits that are unused/available (e.g., for additional lot code bits or the like).

Another example encoded area may use 40 bits, with 4 bits for the version code, 11 bits for the date code (e.g. days from a particular date), 2 bits unused (RFU), 10 bits used for batch identification code, 5 bits used for tray code, and 5 bits used for tray location code.

Accordingly, different bit combinations and arrangements may be used in the encoded area 1024 depending upon the information to be conveyed. In an embodiment, a portion of the encoded area 1024 may kept constant or non-variable, while another portion or portions of the encoded area may be variable. For example, a first portion of the encoded area 1024 may be kept constant for a chemistry type. In an encoded area 1024 kept constant for a chemistry type, the first portion of the encoded area may be kept constant (i.e., have the same pattern or arrangement of bits therein) such that the cuvette is identified as a particular type, for example a cuvette for measuring total chlorine, as opposed to another cuvette type, for example a cuvette for measuring total and free chlorine. The variable portion of the encoded area 1024 may indicate variable information, such as lot information, date information, and the like. A reserved portion of the encoded area 1024 may be the first row of bits encountered by the reader 730 (on a cuvette insertion into the instrument 525), may be the last row of bits encountered by the reader 730, or may be situated elsewhere in a predetermined arrangement/location in the encoded area 1024.

Some non-limiting examples of cuvette encoded areas 1024 and reader 730 arrangements are given below.

Motion Optical Code Example.

An embodiment may read a coded area 1024 from the encoded cuvette 600/700/800 as it is inserted into the instrument 525 and thus past an optical reader 730. The encoded area 1024 may be printed directly to the cuvette, or the encoded area 1024 may be a label that is applied on the cuvette. Example components included in a reader 730 may be as follows: five IR emitting diodes; five IR phototransistors; emitting diode drive circuit; code; and a micro-controller and/or a microprocessor.

An embodiment provides a relatively compact option compared to standard rotating mirror bar code optics. In an embodiment, the lenses of the reader 730 may be small and placed about 4 mm from where the encoded area 1024 will be read. The photodiodes, emitting diodes and micro-controller may also be small to accommodate inclusion within a hand-held mobile instrument 525. An embodiment may use a data encoded area 1024 with timing code (clock bits 1034), with the advantage of that the code can be short in length. A first clock bit 1041 may be included, which may set the timing. If there is skew when the cuvette 500 is inserted, then the clock bits 1034 may not line up with the data bits 1035. Software included in the reader 730 or the instrument 525 may correct for this. An embodiment may use a single encoded area 1024 (clock imbedded) with the advantage that skew is not an issue, but the length of the encoded area 1024 may increase. An embodiment may be made water proof. As the cuvette 500 is inserted, the rate of insertion is not an issue, as described herein. The code may be pre-registered to the cuvette 500, and stored in a memory of the instrument 525.

Static Optical Barcode Example

An embodiment may read an encoded area 1024 from the encoded cuvette 600/700/800 after the cuvette is inserted into the instrument 525. The encoded area 1024 may for example be read when the user starts the instrument 525. Such an embodiment would not need a cuvette detection circuit in the instrument 525. Specific components of the reader 730 may include the following: one IR emitting diode; one linear diode array (128 pixel); an emitting diodes drive circuit; a barcode lense; a barcode mirror; and a micro-controller (10 bit analog to digital). The size of the reader 730 may be dependent on the encoded area's 1024 code print size and the number of bits needed. If a "bit" can be 0.005" (inches) and 32 or 40 bits are used, then the size is relatively small. A side-to-side location of the code may be used to keep the image on the linear array 731 of the reader 730. Such an embodiment has the advantage of being able to read the code when the user presses read on an interface of the instrument 525, so real-time sensing to determine if a cuvette is present may not be required. The linear array 731 may be a single source part. Again the code of the encoded area 1024 may be pre-registered to the cuvette.

Motion Conductive Code Example

An embodiment may include a conductive code in the encoded area 1024 to be read from the encoded cuvette 600/700/800 as it is inserted into the instrument 525. The conductive code may either be printed directly to the cuvette, for example with conductive ink, a conductive label printed with non-conductive ink, or a non-conductive label printed with conductive ink. Specific components of the reader 730 may include the following: small ball bearings; small springs; bearing/spring housings; and a micro-controller. This is a relatively compact option relative to standard rotating mirror bar code optics. The contact may be small and as with other implementations, the micro-controller is small. A data code with timing code may be included in the conductive code, with the advantage that the code can be shorter in length. If there is skew when the cuvette is inserted, then the clock bits 1034 may not line up with the data bits 1035. Software again may correct this. A single code (clock imbedded) may be used with the advantage that skew is not an issue. The length of the encoded area 1024 may increase however.

Magnetic Reader Example

An embodiment may include a magnetic reader head, measurement electronics and a micro-controller in the reader 730. The size may be fairly small, and may depend on the head. In use, a user may insert the cuvette having a magnetic strip into a slot of the instrument 525 at a speed greater than a certain minimum speed. An option is to swipe the cuvette on a magnetic reader that is located elsewhere on the instrument 525 (other than the slot) prior to insertion in the slot of the instrument 525.

Static Conductive Code Example

An embodiment may include the use of a two dimensional (2D) encoded area 1024 printed on a conductive label, similar to the motion code examples described herein.

RFID On-Chip Example

An embodiment may include an RFID tag on the cuvette in the encoded area 1024 with corresponding RFID reader on the instrument 525, e.g., as the reader 730. Once a measurement analysis is completed, the instrument 525 may in turn use the RFID to write information such as results information back to the RFID on the cuvette.

Code on Chip-Associated Component Example

An embodiment may include a code reader 730 on the instrument 525 positioned appropriately so as to read another component, e.g., a box (or other chip/cuvette associated component) that contains the cuvettes, and/or some other type of cuvette identification. Similarly, an RFID tag on a cuvette box may be utilized.

Memory Chip

An embodiment provides that a memory chip may be included on a cuvette, including for example similar information as an encoded area 1024 (and perhaps located in the encoded area 1024), storing the information in digital form to be read by the instrument 525. Memory chips include EPROMS such as Dallas Semiconductor's DS1985F5 16-kbit add-only touch memory device.

Accordingly, various example embodiments have been described wherein the cuvette (or an associated component) may be provisioned with encoded information that is readable by the instrument 525 or other system component. The encoded information provides the system with information regarding the cuvette that is useful for conducting analyses, as well as troubleshooting any potential problems associated therewith. The encoded cuvettes 600/700/800 furthermore relieve the user of the burdensome tasks of managing information regarding the various cuvettes, such as matching them with appropriate slots of the analysis instrument 525 or choosing appropriate routines for chemical analyses.

Cuvette and Sample Cup

Figure 11:
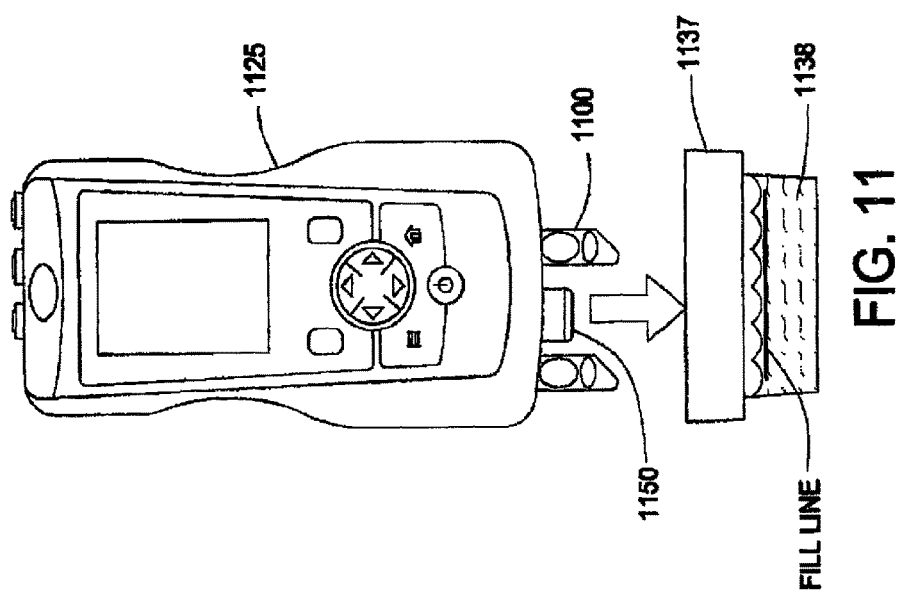
FIG. 11 illustrates an example mobile water analysis instrument with cuvettes installed and sample cup.

Referring to FIG. 11, once inserted, the cuvette 1100 is dipped into fluid sample 1138 and the fluid sample 1138 is drawn into the cuvette 1100 for reaction with one or more reagents for analysis. The cuvette 1100 contains a fluid channel 101 internal thereto (e.g., as illustrated in FIG. 1) that includes necessary chemical(s) in or along the fluid channel 101, as previously described. Accordingly, the cuvette 1100 and fluid channel 101 thereof provide for mixing of the appropriate chemicals for the analysis with a fluid sample 1138 as it is drawn through the fluid channel 101, in one or both directions, by the instrument 1125. The instrument may include a sample detection feature 1150, which provides input to the instrument 1125 confirming that the sample detection feature 1150 has been inserted into fluid sample 1138, e.g., via electrical contact completed by the fluid sample 1138.

Figure 12:
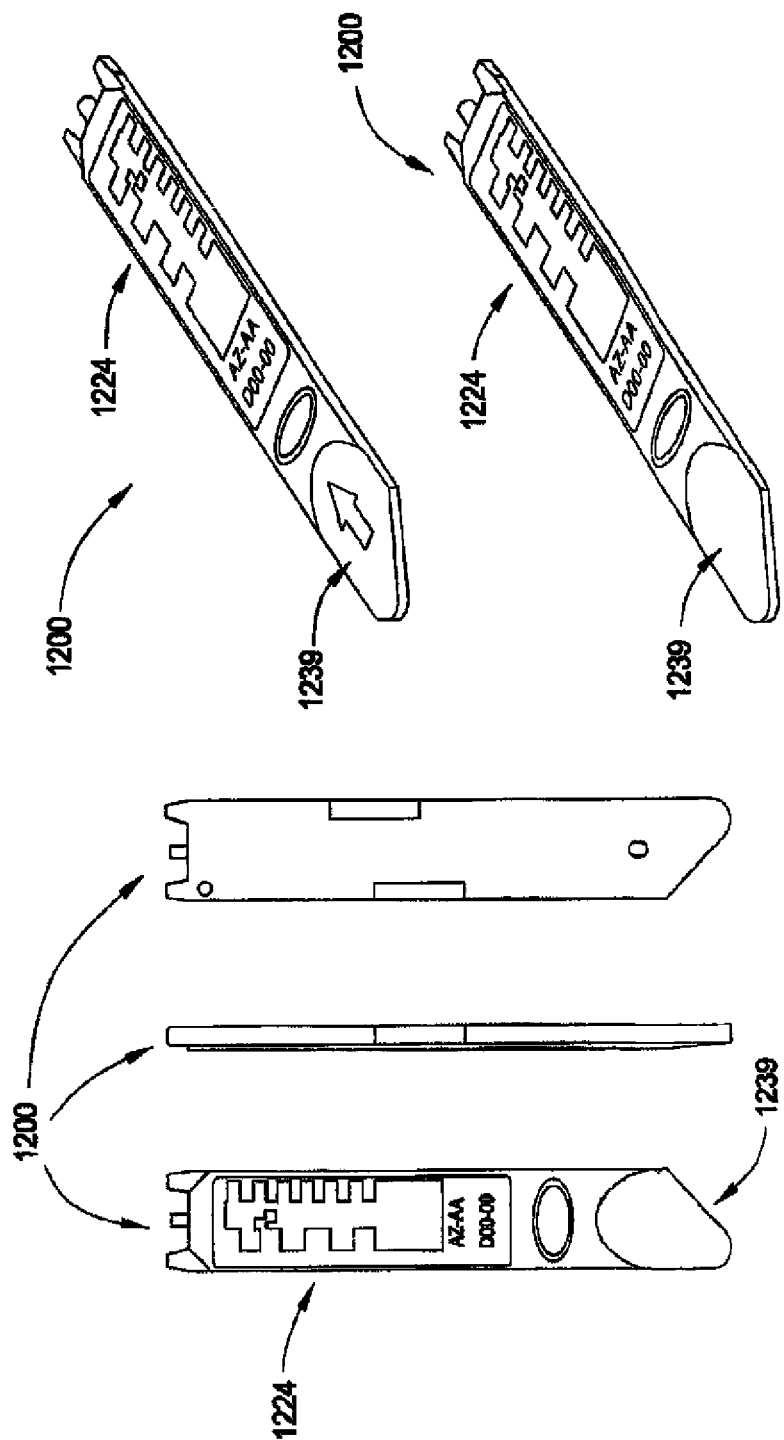
FIG. 12 illustrates example cuvettes having encoded areas and orientation indicators.

As shown in FIG. 12, the cuvette 1200 may contain an encoded area 1224 that is encoded with information that is readable or otherwise interpretable by another component of the system (e.g., the reader 730 of FIG. 7). The encoded area 1124 may convey information including but not limited to information for identifying the type of cuvette 1200 with respect to its chemistry or information conveying which fluid sample movement routine should be executed in connection with the cuvette 1200. The routine may include an appropriate set of program instructions, stored for example in a memory device of the instrument 1125 and executed by one or more processors thereof, such that on execution of the program instructions the fluid sample is moved along the fluid channel 101 in a controlled fashion.

Users may struggle with the correct orientation of the cuvette 1200 for insertion into the instrument 1125. It is possible that the cuvette 1200 could be inserted into the instrument 1125 in any of four orientations, only one of which will afford proper use (e.g., reading of the encoded area 1124 by the instrument 1125, proper intake and analysis of the fluid sample, etc.). Accordingly, two potential difficulties may arise when a user attempts to insert the cuvette 1200 into the instrument 1125; namely, determining which end of the cuvette 1200 goes into the slot of the instrument 1125 and determining which side of the cuvette 1200 is "up" (faces the user). Proper orientation of the cuvette 1200 for insertion is important to the functionality of the system, as the instrument 1125 includes measurements sensors, such as optics 104, for making measurements of the fluid sample when reacted with chemical(s) in the fluid channel 101 of the cuvette 1200, a reader for the encoded area 1124, and the like.

Accordingly, an embodiment provides an orientation feature 1239 that indicates proper insertion for a cuvette 1200. An orientation feature 1239 may include either a textual or a non-textual cue to inform users where they should grasp the cuvette 1200 in order to obtain the proper orientation for insertion into the instrument 1125. The non-textual orientation feature 1139 may be a physical orientation feature or a graphic orientation feature. The non-textual aspect of the orientation feature 1239 ensures that different orientation features need not be translated into different languages, as in the case of a textual cue.

Figure 13:
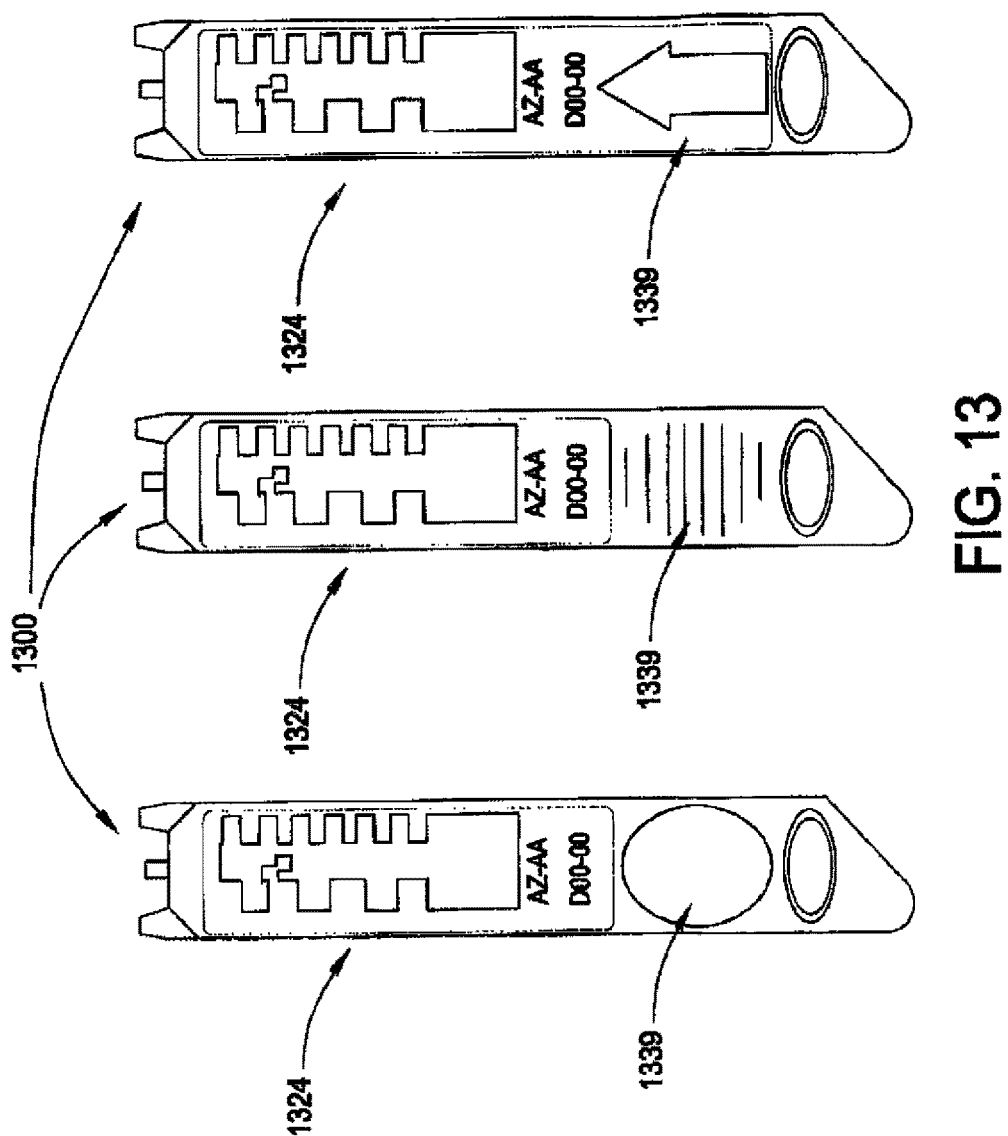
FIG. 13 illustrates example cuvettes having encoded areas and orientation indicators.

In one example embodiment, illustrated in FIG. 12, a non-textual orientation feature 1239 includes a thumb recess or thumb-shaped area of ridges on the top of the cuvette 1200, which provides an instinctive clue that the cuvette 1200 must be grabbed on the proper end (e.g., proximal end of the cuvette 1200), and with the proper side up for insertion of the distal end of the cuvette 1200 into the slot of the instrument 1125. The non-textual orientation feature 1239 may also be a graphic, such as an arrow. A non-textual orientation feature 1239 such as the thumb recess may be molded into the cuvette 1200 and therefore does not increase cost. In some embodiments, more than one non-textual orientation feature 1239 may be included. As illustrated in FIG. 13, the non-textual orientation feature 1339 may include but is not limited to any of the following, either alone or in combination: (1) a recessed thumb-shaped area in a base material of the cuvette 1200; (2) a raised pattern on a base material of the cuvette 1300; and (3) a printed label that may be applied to the base material of the cuvette 1300. In the examples of FIG. 13, the non-textual orientation feature is included in an area outside of the encoded area 1324.

While an orientation feature such as the non-textual orientation features described herein assists the user in obtaining the proper orientation of the cuvette 1100 for insertion into the instrument 1125, the user may experience difficulty in confirming that the cuvette 1100 is properly or fully inserted and secured within a slot of the instrument 1125. Accordingly, an embodiment provides tactile and/or audible feedback cues to the user to confirm that the cuvette 1100 is properly inserted and secured within the instrument 1125.

Figure 14:
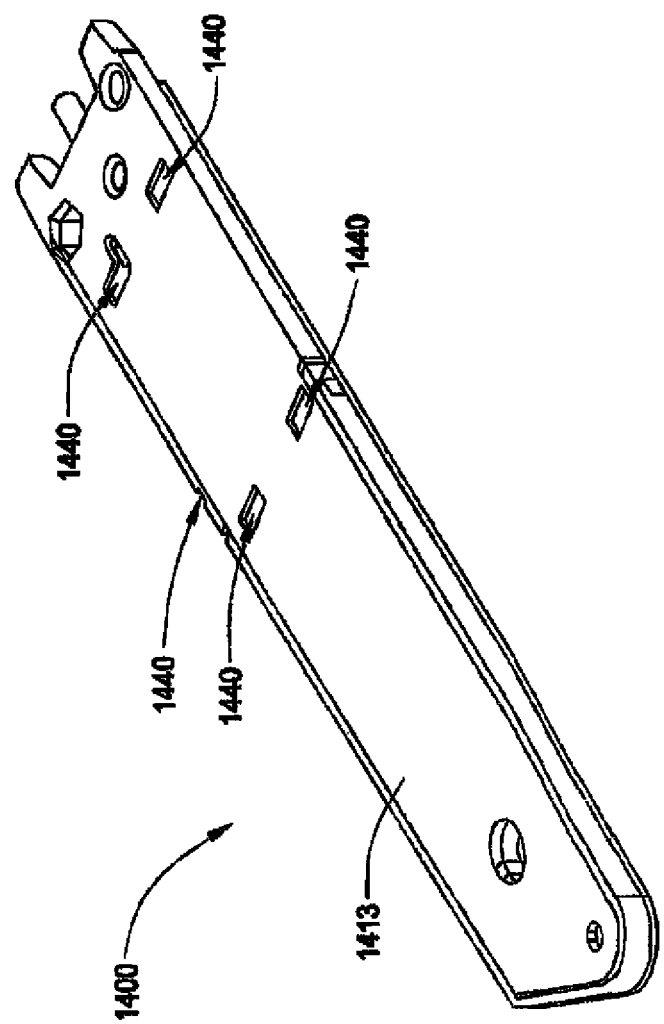
FIG. 14 illustrates an example cuvette having an audible or tactile feedback feature.

Referring to FIG. 14, an embodiment provides a "click-in" feature in the form of recesses 1440 in the body 1413 of the cuvette 1400. This click-in feature 1440 provides a tactile and/or auditory "click" when the cuvette 1400 is fully and properly inserted into a slot of the instrument 525. An embodiment provides one or more recesses for the click-in feature in the cuvette 1400 that are matched to one or more resilient members 1541, referring to FIG. 15(A-B) in a tray 1542. The tray is disposed within the slot of the instrument 525 that receives the cuvette 1400 on insertion. The matching of the recesses 1440 and resilient members 1541 provides that when the cuvette 1400 is properly oriented and inserted into a slot of the instrument 525, the cuvette 1400 and tray 1542 combine to provide a tactile and/or auditory feedback to the user, indicating that the cuvette 1400 has been properly inserted into the tray 1542.

In one example embodiment, the cuvette 1400 contains "top" and "bottom" sides that have a larger area than the "lateral" sides. In one embodiment, four recesses 1440 may be provided to the bottom side of the cuvette 1400, as illustrated in FIG. 14. Four resilient members 1541 are provided in the tray 1542 portion of the slot of the instrument 525, as illustrated in 15A, matching the four recesses 1440 of the cuvette 1400. FIG. 15B illustrates an example assembled tray 1542. Additionally, a recess 1440 may be provided in one or more of the lateral sides of the cuvette 1400, as illustrated in FIG. 14, with a matching resilient member 1541 in the lateral side of the tray 1542, as illustrated in FIG. 15(A-B).

The tray 1542 may be equipped with an element for regulating the temperature of a cuvette 1400. For example, a tray 1542 may include a heating element disposed therein to facilitate heating of a cuvette 1400 inserted into a slot of the instrument 525. The element may be powered using battery power supplied by the instrument 525. A heating element may be used in a tray 1542 for example to increase the overall temperature of the cuvette 1400, such as when outdoor and/or environmental conditions warrant, for example to provide adequate temperature regulation for a chemical reaction within the cuvette 1400 during fluid analysis. Alternatively, the heating element may be molded into the cuvette and may engage contacts within the tray 1542.

In one example embodiment, when the cuvette 1400 is inserted into a slot of the instrument 525, the resilient member 1541 in the tray 1542 matching the recess 1440 in the lateral side of the cuvette 1400 forces or guides the cuvette 1400 into alignment with the four resilient members 1541 in the tray 1542 matching the recesses 1440 in the bottom of the cuvette 1400. Thus, the user is provided with a tactile "click" when the cuvette 1400 is fully inserted in the proper orientation such that the cuvette 1400 "clicks" into place. Additionally, an auditory feedback may be provided by virtue of the type of resilient members/recesses 1400/1541 (and materials thereof) chosen for the tray 1542 and cuvette 1400. Thus, when the resilient member's 1541 "click" and/or "snap" into the recesses 1400, an audible "clicking" sound is provided to the user, along with a tactile click, ensuring the user is provided with multiple levels of feedback indicating proper cuvette 1400 insertion into a slot of the instrument 525. The resilient members 1541 may be formed in a variety of ways. The resilient members 1541 may be leaf springs, or may be ball bearings that are spring loaded, or the like, so long as they provide for a releasable securing mechanism for the cuvette 1400.

FIG. 15A, referred to above, is an exploded version of the tray 1542. Tray 1542 comprises an upper tray 1543 and a lower tray 1540, with a socket 1550 and captivator 1551 shown to the rear and between the upper and lower tray components. Socket 1550 is a partially hollow body that serves to connect in an air-tight fashion to the pneumatic system. Captivator 1551 comprises three individual components, a face plate 1552 and two O-rings that function to seal the cuvette nipple 115 (FIG. 1) to the socket so that an air-tight connection is made upon installation of the cuvette into the tray. Socket 1550 is heat-staked or riveted to both lower and upper tray parts for durability. Upper tray 1543 also has a slot 155 through which light or IR radiation is directed and reflected off of encoded area 724 as the cuvette is slid into the tray.

Referring back to FIG. 11, once the cuvette 1100 has been properly oriented and properly inserted, an embodiment provides a sample cup 1137, illustrated in greater detail in FIG. 16(A-D), to facilitate proper fluid sample collection for chemical analysis with the system. With the cuvette 1100 partially exposed from the instrument 1125, as illustrated in FIG. 11, the cuvette 1100 (the tips thereof) and instrument 1125 are inserted directly into the fluid sample 1138 for 2-3 seconds for fluid sample 1138 collection in the cuvette 1100. A sample detect feature 1150 on the instrument 1100 detects the fluid sample 1138, for example water, initiates fluid sample collection by the instrument 1125, and then alerts the user to remove the cuvette 1100 and instrument 1125 from the fluid sample 1138, whereupon the chemical routine is automatically initiated.

A sample detect feature 1150 of the instrument 1125 ascertains an electrical circuit (or signal) formed via electrical connection of fluid sample 1138 sensitive members, for example contact electrodes disposed within the sample detect feature 1150, being in electrical connection via a conductive fluid sample 1138. The location of the contact electrodes in the sample detect feature 1150 is above that of the opening of the fluid channel within the cuvette 1100 such that the cuvette fluid channel inlet 102 must be submerged within the fluid sample 1138 if the sample detect feature 1150 ascertains a completed electrical circuit. On ascertaining the cuvette 1100 is properly positioned within the fluid sample 1138 via the sample detect feature 1150, the instrument 1100 may indicate or signal as much to the user, for example via light, sound (e.g., speaker, beeper) or otherwise, and begin to draw in fluid sample 1138. If the cuvette 1100 is removed from the fluid sample 1138 prior to an appropriate sample amount being taken up, as sensed for example via the contact electrodes of the sample detect feature 1150 being removed from the fluid sample 1138 and signaling via an appropriate electrical connection to a processor of the instrument 1100, the instrument 1100 may halt the routine, indicate or signal to the user, or a suitable combination thereof.

If the cuvette 1100 remains in the fluid sample 1138 for a full draw of fluid sample 1138 into the fluid channel, the instrument 1125, on completion of the draw of fluid sample 1138, may signal the operator that the fluid sample has been successfully obtained. The user then removes the cuvette 1100 tip(s) from the fluid sample 1138. The instrument 1125 confirms that the cuvette 1100 is no longer placed in the fluid sample 1138, as for example via the contact electrodes of the sample detect feature 1150, and initiates the appropriate predetermined routine of fluid movement routine for the given cuvette 1100 chemistry, as ascertained via user input, cuvette encoded information area 724, or otherwise.

In one embodiment, the instrument 1125 holds four cuvettes 1100, one cuvette 1100 in each of four slots. In one embodiment, in order for the measurements to take place, all inserted cuvettes 1100 plus the sample detect feature 1150 should be in contact with the water sample 1138. In the illustrated example embodiment of FIG. 11, the sample detect feature 1150 is located near or in the center of the four cuvettes 1100.

Users may encounter several issues when asked to perform an analysis of the water sample 1138 with the instrument 1125. Some users are concerned with not getting the instrument 1125 wet and may not recognize the function of the sample detect feature 1150. Therefore, users may attempt to dip only the cuvette 1100 into the sample water 1138, leaving the sample detect feature 1150 on the outside of the sample cup 1137 (out of the sample water 1138). This may lead to a problem of potentially not dipping all four cuvettes 1100 at once, which is ensured if the sample detect feature 1150 is immersed in the sample water 1138, and thus not properly performing the intended measurements.

Accordingly, an embodiment provides a sample cup 1637 that facilitates user training on the instrument, particularly appropriate fluid sample 1138 collection and analysis with the instrument 1125. The sample cup 1637 may generally be formed having two main wall structures 1643, 1644. A first wall structure 1644 forms a narrower bottom of the sample cup 1637 into which the cuvette(s) 1100 may be dipped. A second wall structure 1643 extends from the first wall structure 1644, having a greater cross-sectional area, and thus providing for additional room for accommodating the end of the instrument 1125 into which the cuvette(s) 1100 are inserted. The transition between the first wall structure 1644 and the second wall structure 1643 may be configured to provide a resting area or space 1645 for the end of the instrument 1125 having the cuvette(s) 1100. In other words, the sample cup 1637 is tapered to match the end of the instrument 1125 that contains the cuvette(s) 1100, thus providing a visual cue to the user as to proper insertion. The sample cup 1637 and wall structures thereof 1643, 1644 may be formed of a single, molded piece, for example a single piece of molded plastic.

By providing a custom sample cup 1637, all of the above mentioned problems with sample collection are solved. The sample cup 1637 is shaped to accommodate the end of the instrument 1125 (with cuvettes 1100 inserted), encouraging users to correctly dip the instrument 1125, cuvettes 1100, and sample detect feature 1150 all at once in the sample water 1138. The sample cup 1637 also discourages users from trying to dip just the cuvette 1100 and not the sample detect feature 1150.

A clearly labeled fill line on the sample cup 1637 instructs the users how much sample water 1138 to collect in the sample cup 1637 to facilitate proper sample collection with the instrument 1125 and cuvettes 1100. An overflow hole somewhere above the fill line prevents users from grossly overfilling the sample cup 1637, ensuring that the sample cup 1637 does not overflow.

Although the fill line is included, user may encounter difficulty because of a tendency to fill the sample cup 1637 right up to the top, ignoring the fill line. Of course this is not desirable, as the sample water 1138 may spill out when the instrument 1125 and cuvettes 1100 are properly placed into the sample cup 1637 for sample collection.

Determination of Fluid Sample Location within Test Cuvettes

Figure 17:
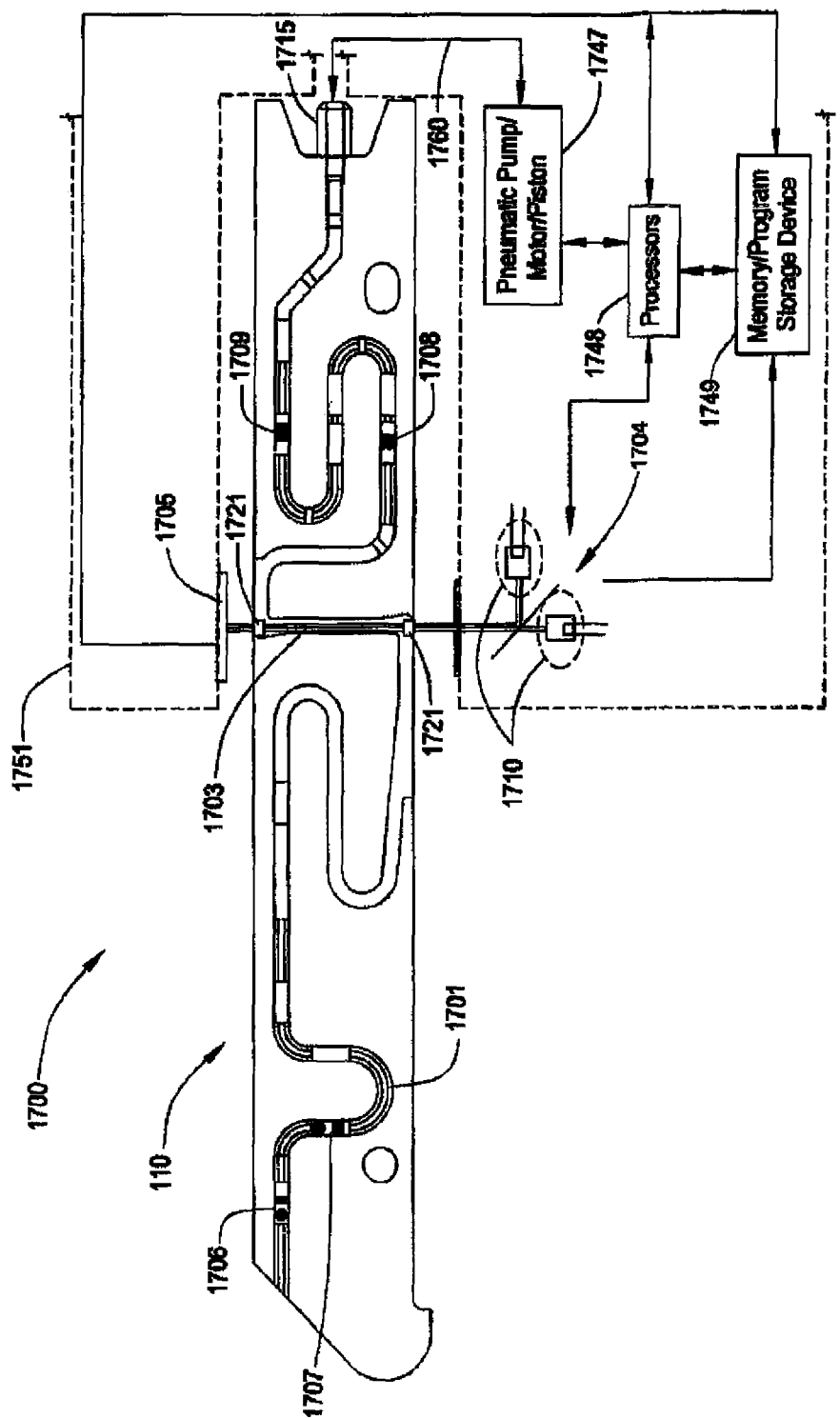
FIG. 17 is a schematic illustration of an example cuvette inserted into an example instrument.

Referring to FIG. 17, the fluid sample may be moved by differential pressure created by the pump arrangement 1747 contained within the body 1751 of the instrument (e.g., instrument 1125) via pneumatic communication between a piston containing chamber of the body 1751 and the fluid channel 101 of the cuvette 1700. Thus, movement of the piston of the pneumatic pump arrangement 1747 within the body 1751 by a motor may decrease or increase pressure/ create a vacuum or positive pressure within the fluid channel 101 in order to displace the fluid sample in a desired direction, e.g., away from the distal end of the cuvette 1700 (having a fluid inlet) and towards the unit body 1751. Additionally, movement in the reverse direction may be accomplished by moving the piston of the pneumatic pump arrangement 1747 in the opposite direction, i.e., creating positive pressure in the fluid channel 101.

As illustrated with a cross-section of a cuvette 1700 in FIG. 17, the fluid sample is reacted with one or more reagents 1706, 1707, 1708, and/or 1709 within a fluid channel 1701 of the cuvette 1700. The fluid sample may be measured in an optical chamber 1703 of the cuvette 1700 (prior to and/or after the fluid sample has encountered/ reacted with reagents 1706, 1707, 1708, and/or 1709). Accordingly, optical measurements may be obtained by the unit body 1751 operating an optics component 1704 (e.g., including light source(s) such as LED(s), diode laser, or the like) on one side of the optical chamber 1703 and sensing/ detecting light at an optical detector component 1705 at the other end of the optical chamber 1703. The light may be transmitted through optical windows 1721 of the cuvette 1700 fitted over each end of optical chamber 1703, or formed integrally into the cuvette body, of the cuvette 1700. Thus, optical windows 1721 provide for light transmission through cuvette 1700 along fluid channel 1701 at optical chamber 1703 for optical measurement.

Optics component 1704 may comprise numerous light sources 1710 depending upon the chromogenic assay at hand. For example, narrow-band emission LEDs of various wavelengths including red, blue and green may be used to illuminate chromophores having certain absorbance bands. Diode lasers may also be used as a source of electromagnetic radiation. Broad-band sources such as a Tungsten lamp may be coupled with filters to select wavelengths used to probe a chromophore. Infra-red emitters may also be used. All of the foregoing may be used alone or in combination with each other, the choice dependent upon the assay/analyte to be detected.

In order to measure optical characteristics of the fluid sample (either before or after reaction with one or more reagents 1706, 1707, 1708, and/or 1709), it is important to accurately and precisely determine the position of the fluid sample within the cuvette 1700 (e.g., in order to determine if the fluid sample has encountered one or more reagents 1706, 1707, 1708, and/or 1709, if the fluid sample has entered or re-entered the optical chamber 1703, etc.).

To accurately and precisely transport and locate an aliquot of fluid sample within the fluid channel 1701 an embodiment provides algorithms for determining the location of the fluid sample within the fluid channel 1701 using optical measurements, for example as obtained via the optical chamber 1703 and associated components.

A displacement pump of a pneumatic pump arrangement 1747 may be used to move an aliquot of fluid sample through the fluid channel 1701 by means of changes in spatial movement of a piston thereof communicated to the fluid sample pneumatically as a change in pressure within the closed volume between the piston and the sample aliquot, as bounded by the fluid channel 1701. In an ideal situation, the change in pressure (with a known volume and known gas/fluid makeup within the fluid channel 1701) may be mapped accurately and with precision to the location of the fluid sample in the fluid channel 1701, such that the location of the fluid sample within the fluid channel 1701 may be determined. Other bi-directional pneumatic pumps may be used to move the air in pneumatic line 1760 to and from socket 1550 thereby moving air into and out of the fluid channel 1701. Other well-known bi-directional pump types include diaphragm, peristaltic, magnetostrictive, and similar pneumatic pumps, which are well-know to one of ordinary skill and thereby come within the scope of this disclosure. Accordingly, an embodiment provides methods and devices to accurately determine the position or location of the fluid sample within the fluid channel 1701 (including the optical chamber 1703 portion thereof), and ensures that variability of location of the fluid sample may be accurately determined and taken into account prior to attempting to measure or characterize the fluid sample via the optical chamber 1703.

In an embodiment, the cuvette 1700 includes an optical chamber 1703 in the fluid channel 1701 used for example for determination of the concentration of a constituent of the fluid sample (e.g., determination of chlorine concentration via colorimetric assay, although other measurements may be made). An embodiment utilizes the optical chamber 1703 (and related components) to determine changes in location of the fluid sample, e.g., by detecting the presence or absence of fluid sample in the optical chamber 1703.

Figure 18:
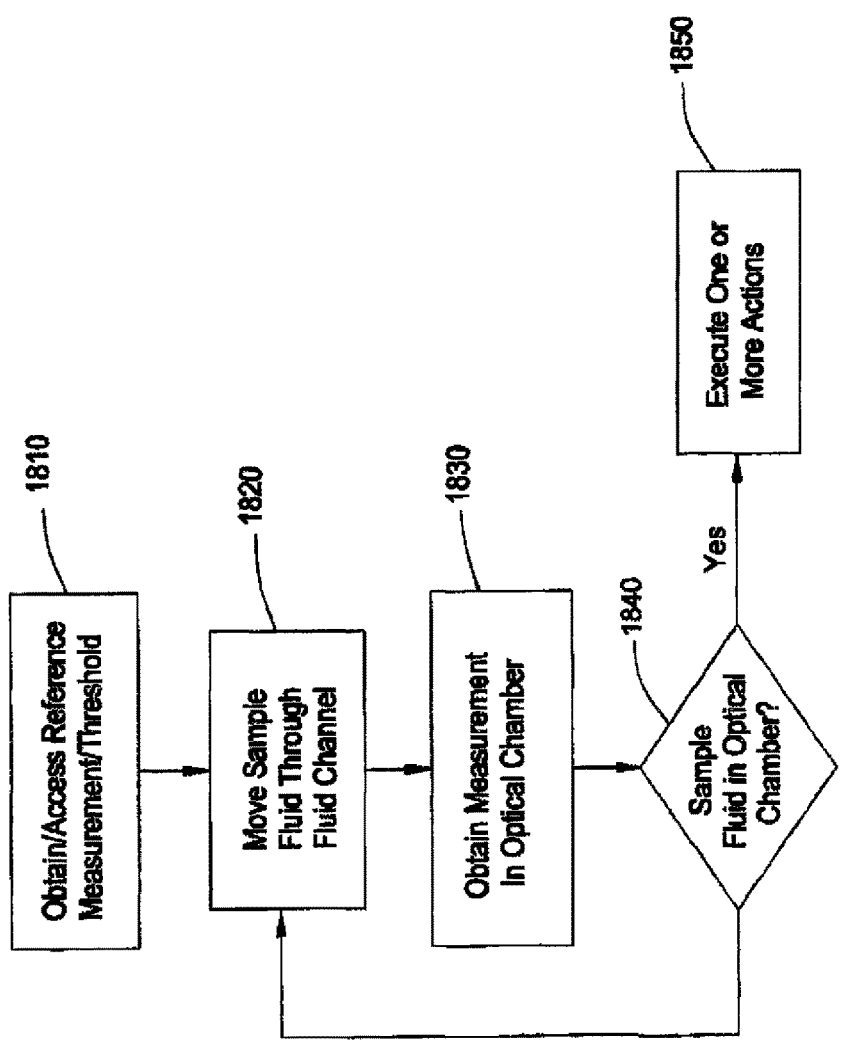
FIG. 18 illustrates an example method of determining fluid sample location in a cuvette.

For example, referring generally to FIG. 18, when the leading edge of the fluid sample moves into the optical chamber 1703 the fluid interface between the gas and fluid sample is distorted due to surface tension and pressure acting on the gas/fluid interface. This results in a non-planar shape of the interface, which in turn results in detectable refraction of the light impinging upon the gas-to-liquid interface. This results in a change in the direction of the light transmitted through the optical chamber 1703 (as compared to a reference measurement, obtained when no fluid sample is contained within the optical chamber 1703 or via a predetermined expected measurement stored for example in a memory 1749 of the body 1751).

Accordingly, when the gas/fluid interface enters the optical chamber 1703, the light that would normally (in the absence of the gas/fluid interface) pass directly through the optical chamber 1703 is distorted in a way detectable by a detector component 1705 (disposed at an opposing side of the optical chamber 1703). Accordingly, an embodiment may utilize a light detector 1705 (or like component) to detect the liquid/gas interface reduction in light and utilize this information (alone or in combination with related information, e.g. fluid sample size, cross sectional area of the fluid channel 1701, etc.) to determine a location/position of the fluid sample within the fluid channel 1701.

In an embodiment, at 1810 a reference measurement, for example via a measurement obtained prior to the fluid sample transport to optical chamber 1703 (i.e., a measure of the optical transmission is made without fluid sample present in the optical chamber 1703). Alternatively or in addition, a predetermined threshold value, for example as stored in a memory device 1749 may be obtained.

Next at 1820, the fluid sample is transported or moved along the fluid channel 1701 towards the optical chamber 1703, e.g., by an incremental displacement of a piston of a pneumatic pump arrangement 1747 located within the body 1751. For one or more of the incremental movements of the piston, and corresponding movement of the fluid sample within the fluid channel 1701, a new measurement of the optical transmission may be made within the optical chamber 1703 for comparison with the original reference measurement or predetermined threshold value at 1830. This process of repeated measuring may be iterated until one or more measurements indicate the presence of the fluid sample within the optical chamber 1703 at step 1840. In response to detecting the fluid sample in the optical chamber at 1830, one or more actions may be executed at 1850. For example, the volume of the fluid sample may be determined, a warning indication may be given to the user if the fluid sample volume or position are not as expected (e.g., based on comparison to known values), the fluid sample may be automatically repositioned by altering the fluid movement routine, etc.

Thus, in an embodiment, the movement routine of the fluid sample within the fluid channel 1701 may be modified based on information regarding the location of the fluid sample within the fluid channel 1701 and/or other attributes of the fluid sample. As an example, a fluid sample aliquot may be repositioned as a result of it not being located in an expected position. Moreover, an error or warning indication may be given, for example in response to determining the fluid sample aliquot is not of an expected volume.

The volume of the fluid sample aliquot may be determined as follows. The length of a particular fluid sample aliquot may be determined using the determined location of the fluid sample and a known cross-sectional area of the fluid channel 1701. This may be accomplished in response to ascertaining slope changes in optical measurement or Relative Standard Deviation (RSD) change in transmission measurements that are correlated to incremental movements of the pneumatic displacement pump 1747 of the body 1751 that detect a leading edge of the fluid sample in the optical chamber 1703. Each incremental movement of the pneumatic pump is proportional to a corresponding incremental displacement by volume of the aliquot within fluid channel 1701. The lagging edge of the fluid sample may be similarly found, for example by estimating its location using the fluid sample volume, the volume of the fluid channel 1701, and the location of the fluid sample's leading edge; or the lagging edge may be found by optical detection in a similar fashion as the leading edge detection as described herein. Thus, the lagging edge of the aliquot of fluid sample may be detected by optical measurements coordinated with the lagging edge of the fluid sample exiting and/or re-entering the optical chamber 1703 (in the case of reverse directional flow of the fluid sample aliquot). The volume of the aliquot of fluid sample may therefore be determined by summing the incremental movements of the pneumatic pump from detection of the leading edge to detection of the lagging edge of the aliquot and correlating the total incremental movements to a total volume of the aliquot.

Embodiments therefore provide means for determining the location of a fluid sample with a testing cuvette 1700. Based on the determined position of the fluid sample within the cuvette 1700, one or more additional determinations (e.g., fluid sample aliquot volume) may be made, and one or more actions may be taken (e.g., modification of the fluid sample movement routine, providing an indication to the user regarding a potential problem or lack thereof, etc.).

Moreover, the system may include or have access to a library of instructions (for execution to accomplish fluid sample movement routines), and the system may select an appropriate set of instructions from the library based upon the type of cuvette 1700 that has been inserted into a slot of the instrument 1751. The instruction set chosen for a particular type of cuvette 1700, e.g., a total chlorine measurement cuvette, will be coordinated to move the fluid sample throughout the fluid channel 1701 based on knowing exactly where on the cuvette 1700 fluid channel 1701 the reagents 1706, 1707, 1708, and/or 1709 are placed. Once the system determines the type of measurement that needs to be performed and the leading edge of the fluid sample is found, the system can utilize the pump arrangement 1747 used to find the leading edge (which may be dedicated to a particular cuvette of the multiple cuvettes inserted into the instrument 1751) to move the fluid sample to the reagent locations 1706, 1707, 1708, and/or 1709 according to the desired sequence, timing, mixing, etc.

As fluid samples are typically transported by means of direct contact of the fluid sample with a piston (e.g., a plunger in a syringe of the displacement pump), the direct contact of the fluid sample to the piston may result in carry-over of the previous sample adhering to the piston. If the piston is not replaced or cleaned between subsequent sampling operations contamination of subsequent samples due to carry-over may result. Embodiments therefore allow re-use of the piston/displacement pump, e.g., as for example located in the body 1751, rather than provisioning a disposable piston and/or other components. This is accomplished for example by eliminating any direct contact between the fluid sample and the displacement pump components 1747 (e.g., a piston thereof) via the inclusion of an intermediate gas phase between the piston and the fluid sample disposed within the fluid channel 1701. Using embodiments, the intermediate gas phase may be used to communicate to the fluid while maintaining the ability to accurately locate the position/location of the sample aliquot within the cuvette's fluid channel 1701 and make appropriate ancillary determinations and/or take appropriate remedial actions, if necessary.

Figure 18B:
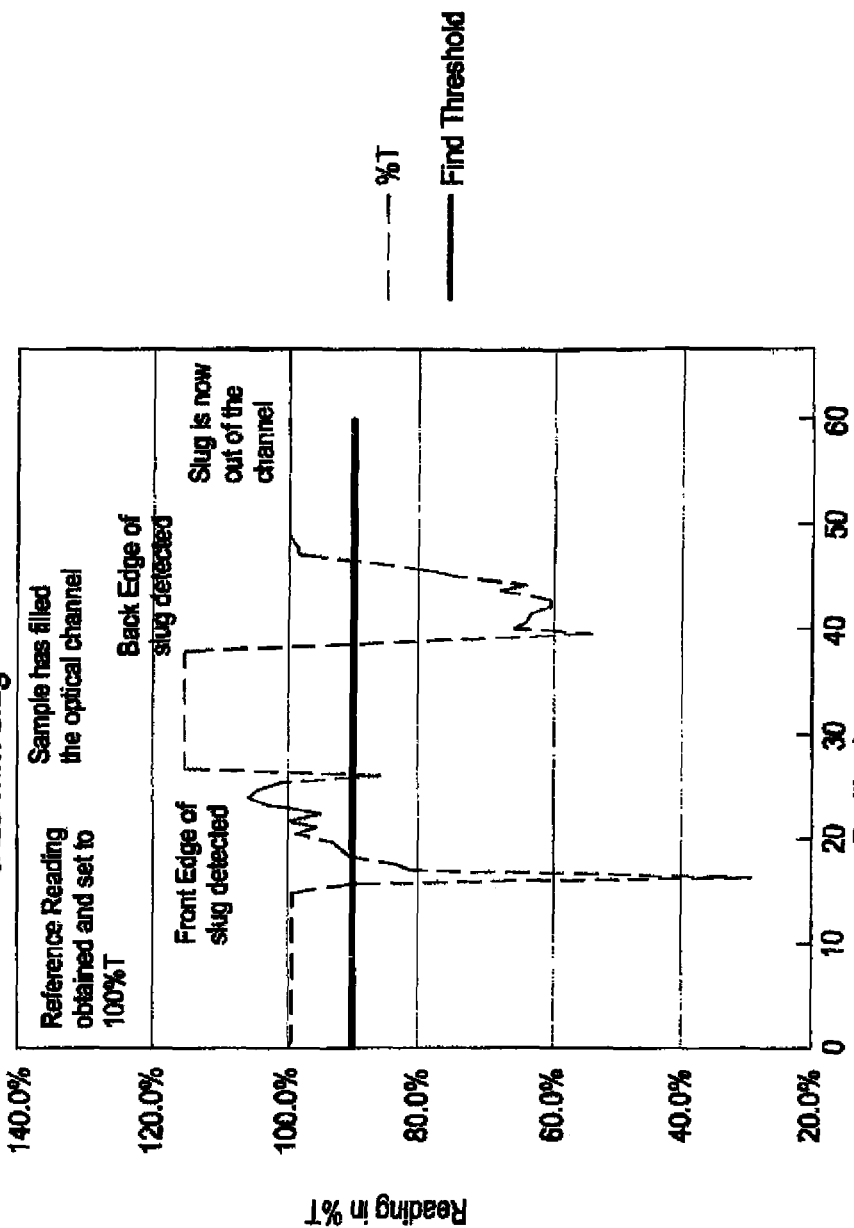
FIG. 18B illustrates an example of measurement data by position of the chip with a 23 mm slug.

FIG. 18B is a graph plotting % Transmission of light down optical chamber 1703 against position of the sample slug in the chamber in millimeters (mm). There is a first discontinuity when the air in optical chamber 1703 begins to be replaced by the liquid front of the sample. Transmission decreases from approximately 100% to 30% over a 1-2 mm distance, and then recovers rapidly at around the 25 mm mark as the liquid slug fills the optical chamber. As it continues to traverse the chamber the back end of the slug becomes detectable at around the 40 mm marks the transmission again falls off rapidly. As the slug leaves the chamber the transmission returns to the baseline 100%. There transitions are reliable and repeatable, and provide a novel method for tracking the front and rear edges of the slug as it traverses the cuvette.

It will be readily understood that various embodiments may be implemented using any of a wide variety of devices or combinations of devices, for example for determining the location of a sample fluid within a fluid channel of a cuvette, movement of a sample within a cuvette, optical analyses and measurements of fluid sample within a cuvette, or other functionality as described herein. An example device that may be used in implementing embodiments includes a device in the form of system or instrument, as described herein, incorporating a body unit 1751 having one or more processors 1748 and program code stored in memory or non-signal program storage device 1749. In this regard, a processor 1748 may execute program instructions/code configured to operate optical transmission and detection components, operate a pneumatic pump arrangement, calculate estimated sample fluid location/position/volume, perform optical analyses on colored fluid samples, or perform other functionality of the embodiments, as described herein. Accordingly, the system or instrument may represent a portable water analytical instrument with appropriate circuitry and logic for performing the functions described herein.

Components of instrument may include, but are not limited to, at least one processing unit 1748, a memory 1749, and a communication bus or communication means that couples various components including the memory 1749 to the processing unit(s) 1748. The system or instrument may include or have access to a variety of device readable media. The system memory 1749 may include device readable storage media in the form of volatile and/or nonvolatile memory such as read only memory (ROM) and/or random access memory (RAM). By way of example, and not limitation, system memory 1749 may also include an operating system, application programs, other program modules, and program data.

In the example of a portable water analytical instrument, a user may interface with (for example, enter commands and information) the instrument through input devices. A display device can also be included with the instrument. In addition to a display device, the instrument may also include other input and/or output devices, e.g., analog and/or digital/logical. The instrument may operate in a networked or distributed environment using logical connections to other devices or databases. The devices may use logical connections with the instrument, and the logical connections may include a network, such local area network (LAN) or a wide area network (WAN), or wireless networks, but may also include other networks/buses.

As will be appreciated by one skilled in the art, aspects may be embodied as a system, method or program product. Accordingly, aspects may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

Any combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device.

Micro-Fluidic Cuvette

Figure 19:
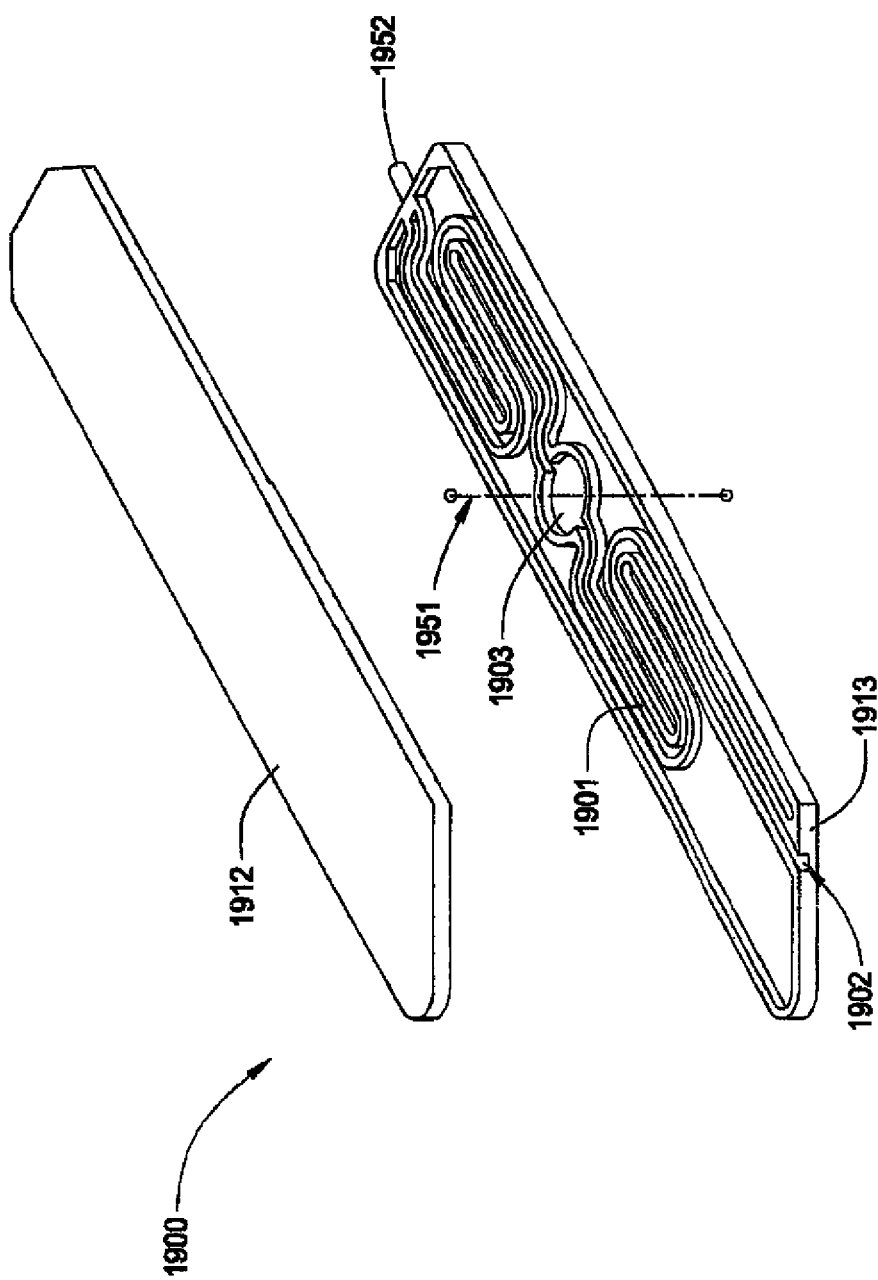
FIG. 19 illustrates a cuvette assembly, diametric view with a circular optical chamber wherein light propagates the thickness of micro-fluidic cuvette.

A common means to facilitate optical measurements in a micro-fluidic cuvette, as example micro-fluidic cuvette 1900 of FIG. 19, is to transmit and measure the changes in electromagnetic radiation, (hereafter generally referred to as 'light' for simplification but is understood that the teachings here within are not limited to the visible portion of the electromagnetic spectrum), through the thickness of the cuvette 1900 comprised of a body 1913 and lid 1912; i.e., the optical path length is determined by the internal thickness of the optical chamber 1903 as shown in FIG. 19. Light traverses the micro-fluidic cuvette along optical axis 1951 through optical chamber 1903. Liquid sample is drawn into the fluidic pipe inlet 1902 formed by the bonding lid 1912 to the fluidic channel of body 1913, e.g., by means of differential pressure exerted between inlet 1902 and orifice 1952. Optical chamber 1903 may be formed of a thin cylindrical cavity created by an expansion of fluid channel 1901. Although light is easily presented and collected through the optical chamber 1903 due to the expansion of the fluid channel 1901 at the optical chamber 1903, the path length is relatively short which reduces the sensitivity of the optical measurement or absorbance measurement in accordance with established principles Beer-Lambert wherein the absorbance through a material is directly related to the path length by;

$$A = \varepsilon \cdot b \cdot c \tag{1}$$

where A is the absorbance, $\varepsilon$ is molar absorptivity of the material, b is the path length and c is the concentration of the analyte. The absorbance value is related to the light transmittance of a material by:

$$A = -\log_{10} \cdot \frac{I}{I_0} \tag{2}$$

where $I_0$ is the incident energy, (intensity of incident light) and I is the energy transmitted through the material, (intensity of the transmitted light).

To improve the sensitivity of the measurement the optical path length b or the concentration c of the analyte may be increased. Wherein the concentration of the material is the independent variable, the path length may be increased to improve the sensitivity of the measurement.

Figure 20:
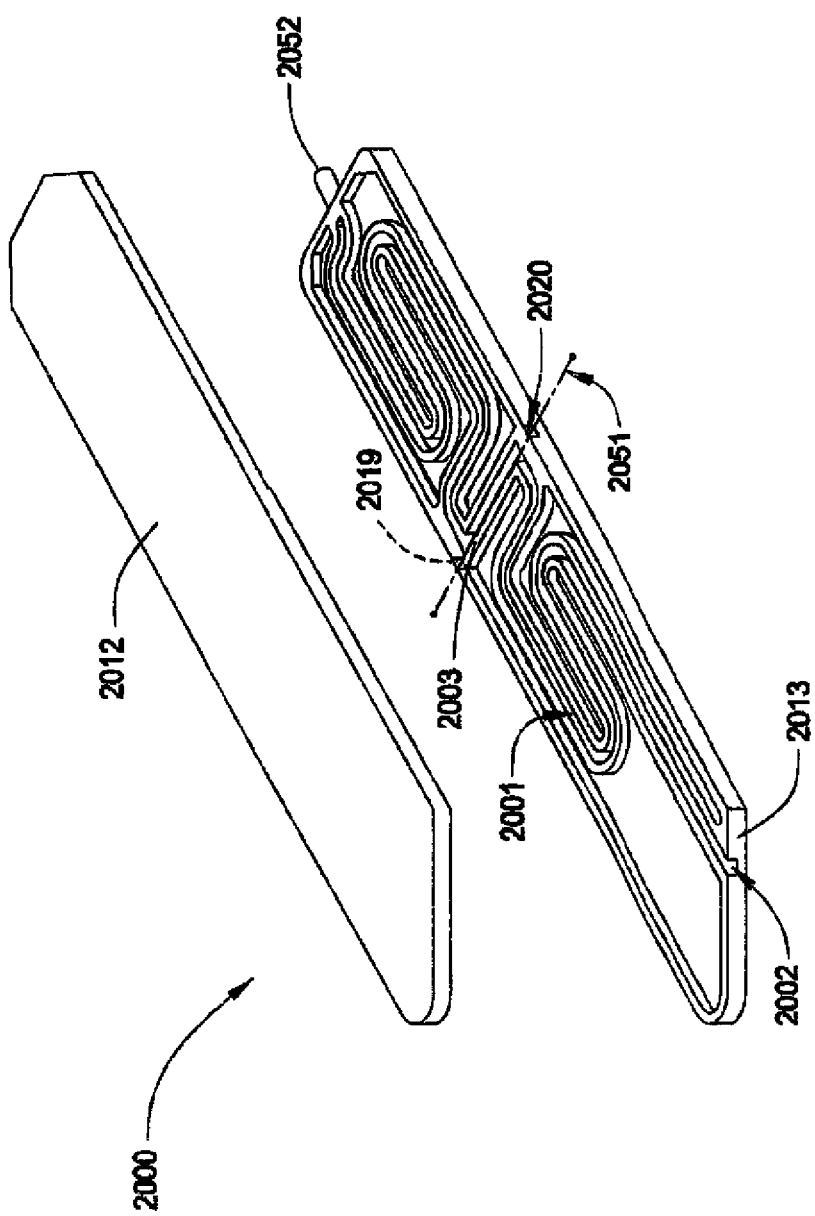
FIG. 20 illustrates a cuvette assembly, diametric view wherein light propagates the width of a micro-fluidic cuvette.

The cuvette 2000 of FIG. 20 realizes an increase in the path length by the transmission of light through the width of the cuvette 2000. Entrapped air or an air bubble present within the optical chamber 2003 of the micro-fluidic cuvette 2000 interferes with the absorbance measurement by scattering the light transmitted through the cuvette. If fluid remains in the optical chamber 2003 after fluid has been transported out of optical chamber 2003, it interferes with the determination of the fluid presence or position of the fluid within the optical chamber 2003.

Entrapped air may occur within the optical chamber 2003 of FIG. 20 due to a lack of contact or lack of wetting between the sample fluid and the fluidic channel 2001 as liquid is transported along the fluidic channel 2001. Specifically there are areas of the optical chamber 2003 that remain un-swept during the transport of fluid within optical chamber 2003 due to the specific geometric features used for the unimpeded transmission of light through the optical chamber 2003, i.e., an optical chamber 2003 comprised of flat windows 2019 and 2020 or otherwise described as planar optical surfaces placed at each end of optical chamber 2003 through which light enters through a first window, interacts with the fluid within the optical chamber 2003 and exits the optical chamber 2003 through a second window along optical axis 2051.

Figure 21:
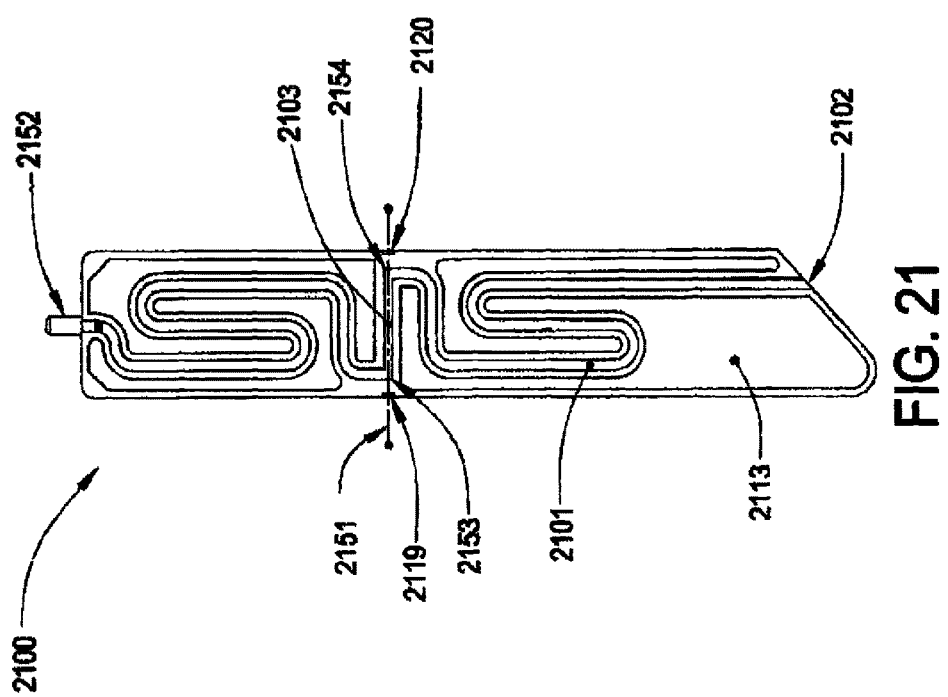
FIG. 21 illustrates a cuvette substrate top view of an optical chamber with sharp corners.

An optical chamber comprised of flat windows, or planar optical surfaces and an enclosed fluidic channel 2001 or square/rectangular pipe forms sharp corners where the flow of fluid through the optical chamber 2003 abruptly changes directions at the face of the planar optical surface as shown in FIG. 21. That is, for example wherein the fluidic channel 2101 makes an abrupt bend at corners 2153 and 2154 of optical chamber 2103. Differential pressure between the inlet 2102 and orifice 2152 of the micro-fluidic cuvette 2100 exerts a force upon the fluid within the fluid channel 2101 and optical chamber 2103 which causes the fluid to move along the fluid channel 2101 as long as sufficient differential pressure is applied to overcome opposing resistive forces such as gravity, viscosity or surface attraction.

Not wishing to be held to any particular theory, it is currently believed that attraction between atoms of solid surfaces, body 1913 and lid 1912 and the atoms of the liquid inside fluid channel 2101 and optical chamber 2103 create a static condition wherein the atoms are essentially immobile at the liquid/solid interface or boundary layer. The viscosity of a liquid is the result to the inter-molecular attraction of atoms within the fluid. A liquid forced to move through a fluid channel 2101 by application of a differential pressure causes the gas/fluid interface to exhibit a convex shape, protruding towards the low pressure side of the gas/liquid interface as layers of the liquid adjacent to the boundary layer are sheered as the fluid is forced through fluid channel 2101 and optical chamber 2101. As the convex gas/liquid phase interface approaches corner 2153 and/or 2154, the gas/liquid interface comes in contact with the planar structures of the corner 2153 and/or 2154 before the interface can reach the apex thus entrapping a volume of gas within the corner.

The volume of gas entrapped within the corner 2153 and/or 2154 is largely dependent on the viscosity and the velocity of the fluid. The entrapped gas may take the form of a bubble or meniscus within corner 2153 and/or 2154. The shape and size of the entrapped gas is naturally inconsistent due to a wide variety of variables, some of which are, as example; homogeneity variations within the fluid, small variations in construction details of the optical chamber 2103, changes in the velocity of the fluid, inconsistency of the surface charges of the construction materials and the random molecular activity in the atoms of the fluid. Light which would otherwise traverse optical chamber 2103 in a direct path when no entrapped gas is present in corner 2153 and/or 2154 with liquid present within the optical chamber 2103 is refracted and partially reflected by the presence of the curved gas/liquid interface of the entrapped volume of gas within corner 2153 and/or 2154. The inconsistency of the volume of the entrapped gas creates a variable error in the measurement whereby the expected transmission differs from the actual transmission of light through the optical chamber 2103 from one micro-fluidic cuvette 2100 to another or one measurement to the next.

Liquid which remains within corners 2153 and/or 2154 of optical chamber 2103 of FIG. 21 after the fluid has been transported out of the optical chamber 2103 is likewise problematic. Similar to the entrapment of air within the corners of the optical chamber, a meniscus of fluid can bridge the walls or windows forming the corner which captures the fluid by means of capillary action due to a concentration of surface attraction within a corner structure and the nature of a fluid to minimize the surface area in contact with a solid due to mutual charge within the fluid. Light which would otherwise traverse optical chamber 2103 in a direct path when no fluid is present in the corner of the optical chamber 2103 is refracted by the presence of the curved gas/liquid interface of the entrapped volume fluid within corner 2153 and/or 2154 resulting in an error when the transmission of light through optical chamber 2103 obtained prior to introduction of the fluid into the optical chamber 2103 is compared to the result obtained after the fluid is removed from the optical chamber 2103 and that result is different.

The error due to the presence of fluid in corner 2153 and/or 2154 of optical chamber 2103 can create a situation which makes it difficult to detect the presence or absence of fluid within the optical chamber 2103 or reestablish a measurement baseline with no liquid present. Without knowing with certainty if the fluid is correctly positioned completely within the optical chamber 2103, (i.e., the optical chamber 2103 is completely filled), inconsistency in the light measurements taken through the optical chamber 2103 will result from an undefined path length and loss of light due to reflection and/or refraction due to the presence of a gas/liquid interface of the partially filled optical chamber 2103.

In addition, the volume of retained fluid in corners 2153 and/or 2154 of optical chamber 2103 varies as the fluid is subsequently re-introduced and removed from the optical chamber 2103 due to the variations previous described for variation of the entrapped gas volume. A method that is dependent on the differential measure of light transmitted through a micro-fluidic cuvette 2100 with the fluid present within the optical chamber 2100 as compared to a measure of light transmitted through a micro-fluidic cuvette 2100 after the fluid is removed can produce an erroneous result when fluid is retained within measurement portion of the optical chamber 2103.

A micro-fluidic cuvette 2103 which minimizes the errors due to entrapment of gas or residual presence of fluid does so by modifying the shape and/or volume of the corner structure of a micro-fluidic cuvette 2103 to reposition the corner 2153 and/or 2154 beyond the measurement portion of the optical chamber 2103. With the repositioned corner structure, light which is transmitted through the optical chamber 2103 does not encounter the entrapped gas or residual fluid presence. To a similar result the measurement portion of the optical chamber 2103 can be reduced by use of an aperture to eliminate the transmission of light through the sharp corner of the micro-fluidic cuvette 2100.

Such mitigation strategies may not be completely successful. Modification of the corner structure of the optical chamber 2100 can have detrimental consequences such as partitioning of the liquid within the optical chamber 2100 due to abrupt cross-sectional changes in the velocity of the fluid as the fluid makes strategic maneuvers about the modified corner structure or limits the velocity at which the fluid can be transported through the optical chamber 2100. Reducing the measurement portion of the optical chamber 2100 by use of an aperture results in a loss in the incident light intensity and throughput since a portion of the light that would otherwise traverse the optical chamber 2100 without the aperture is obstructed. As the amount incident light is reduced the quantification and/or range over which the concentration of the analyte can be determined is limited by systematic noise per equations {1} and {2}; (i.e., the signal-to-noise ratio (SNR) is decreased for a given system noise wherein both $I_0$ and I are subject to quantization uncertainty due to the presence of noise).

An embodiment mitigates error due to unintentional refraction of light transmitted through the optical chamber of a micro-fluidic cuvette due to the entrapment of gas and/or retention of fluid within the optical chamber. Entrapped gas and/or retention of fluid within the optical chamber are mitigated by eliminating the need for the fluid to make strategic maneuvers within the optical chamber and by altering the optical ray path through the optical chamber by means of Total Internal Reflection (TIR) within the substrate and modification of enclosing structure of the micro-fluidic cuvette resulting in a constant fluidic cross-section with no oblique or sharp bends along the fluid pathway.

Furthermore, an embodiment provides modifications to the substrate and/or enclosing structure to confine the propagation of light to the optical chamber as the light travels from one end of the optical chamber to the opposing end.

Moreover, an embodiment improves the ability to detect the presence or absence of liquid within the optical chamber of a micro-fluidic cuvette by increasing the number of surface reflections for light propagating the optical chamber and/or by preventing light from directly transmitting through the optical chamber in the absence of liquid.

Figure 22:
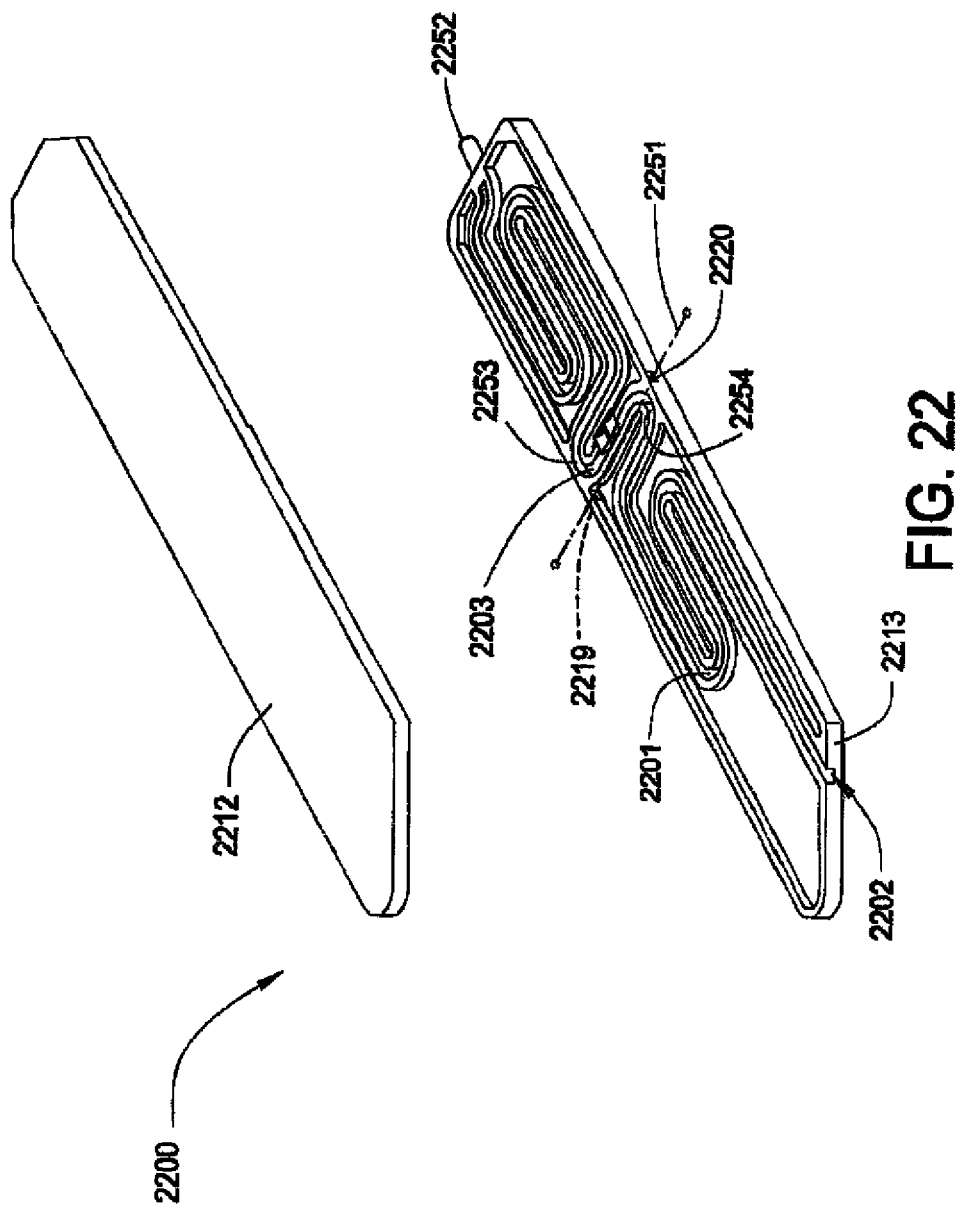
FIG. 22 illustrates in a diametric view a cuvette assembly.

Referring to FIG. 22 one embodiment of micro-fluid cuvette 2200 is comprised of body 2213 and lid 2212. Incorporated into body 2213, a fluid communication nipple 2252, optical surfaces 2219 and 2220 for the transmission of light into and out of body 2213 along optical axis 2251. Body 2213 and lid 2212 are bonded to one another by weld, adhesive or other joining means to form fluid channel 2201, optical chamber 2203 and fluid communication orifice 2252. Micro-fluidic cuvette 2200 comprised of body 2213 to lid 2212 forms a continuous fluid channel 2201 able to communicate a fluid internally by means of differential pressure exerted between inlet 2202 to orifice 2252 through fluid channel 2201 and including optical chamber 2203.

The fluid channel 2201 of micro-fluidic cuvette 2200 provides a smooth communication path for the flow through optical chamber 2203 by means of radial bends at each end of the optical chamber 2203 shown as radial bends 2253 and 2254.

The optical axis 2251 and optical chamber 2203 of micro-fluidic cuvette 2200 are separate. Optical axis 2251 of micro-fluidic cuvette 2200, (and by association optical surfaces 2219 and 2220 which pierce optical axis 2251), are located within body 2213 adjacent optical chamber 2203. This is illustrated in the cross sectional view of FIG. 24.

Figure 23:
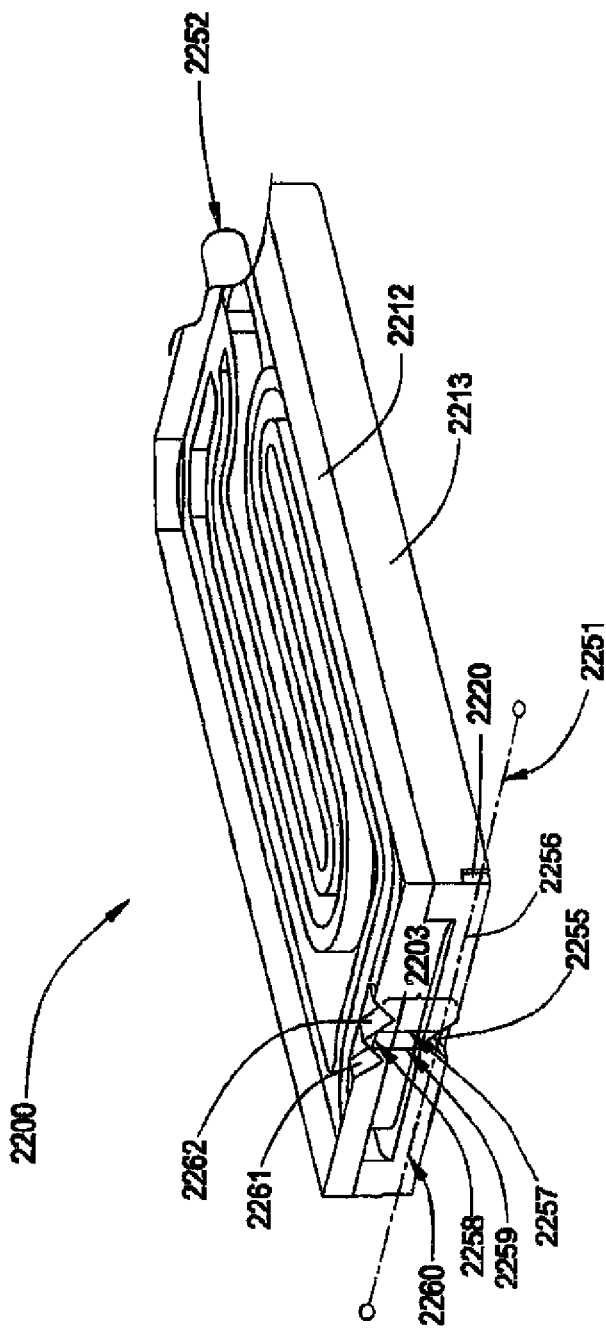
FIG. 23 illustrates a cross-sectional, diametric view of FIG. 22 with a light path resulting from TIR traversing the optical chamber twice.

Cross sectional view FIG. 23 depicts light transmitted along optical axis 2251 which interacts with optical chamber 2203. Optical feature 2255 (shown in this embodiment as a triangular feature) is formed in body 2213 as two conjoined right-angle optical surfaces that intersect optical axis 2251 along ray path segment 2256 collinear with optical axis 2251 at 45 degrees internal to body 2213. Ray path 2256 is totally internally reflected (TIR) and redirected along ray segment 2257 perpendicular to ray segment 2256 so as to pass through optical chamber 2203, perpendicular to the flow of fluid and beyond radial bends 2253 and/or 2254 of FIG. 22. Ray segment 2257 is likewise internally reflected and redirected by optical feature 2262 and 2261 incorporated in lid 2212 as ray segments 2258 and 2259, resulting in ray segment 2459 again traversing optical chamber 2203 perpendicular to the flow of fluid to impinge upon the second surface of optical feature 2255 of body 2213. Optical feature 2255 internally reflects and redirects ray segment perpendicular to ray segment 2258 as ray segment 2260 collinear with optical axis 2151.

Total internal reflection occurs at the boundary between two conjoined materials of different refractive indices for a ray propagating within a second material with refractive index relatively higher than that of the first material to which the ray is propagating towards and impinges upon the boundary at an angle exceeding the critical angle, (i.e., the angle of refraction is equal to or exceeds 90 degrees), per Snell's Law:

$$n_1 \sin(90) = n_2 \sin(\theta c) \quad \{3\}$$

where $n_1$ is the refractive index of a material lower than $n_2$, $n_2$ is the refractive index of a material higher than $n_1$ and $\theta_c$ is the critical angle.

Figure 24:
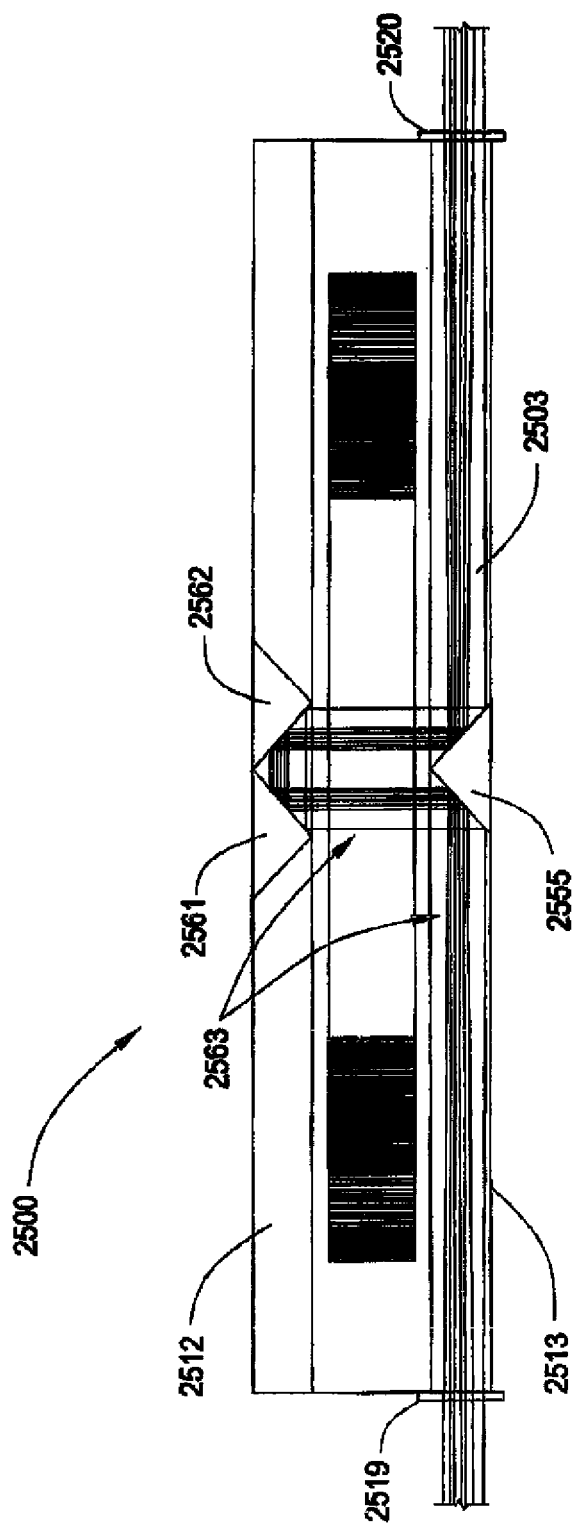
FIG. 24 illustrates a cross-sectional view of FIG. 22 with a ray trace resulting from TIR traversing the optical chamber twice.
Figure 25:
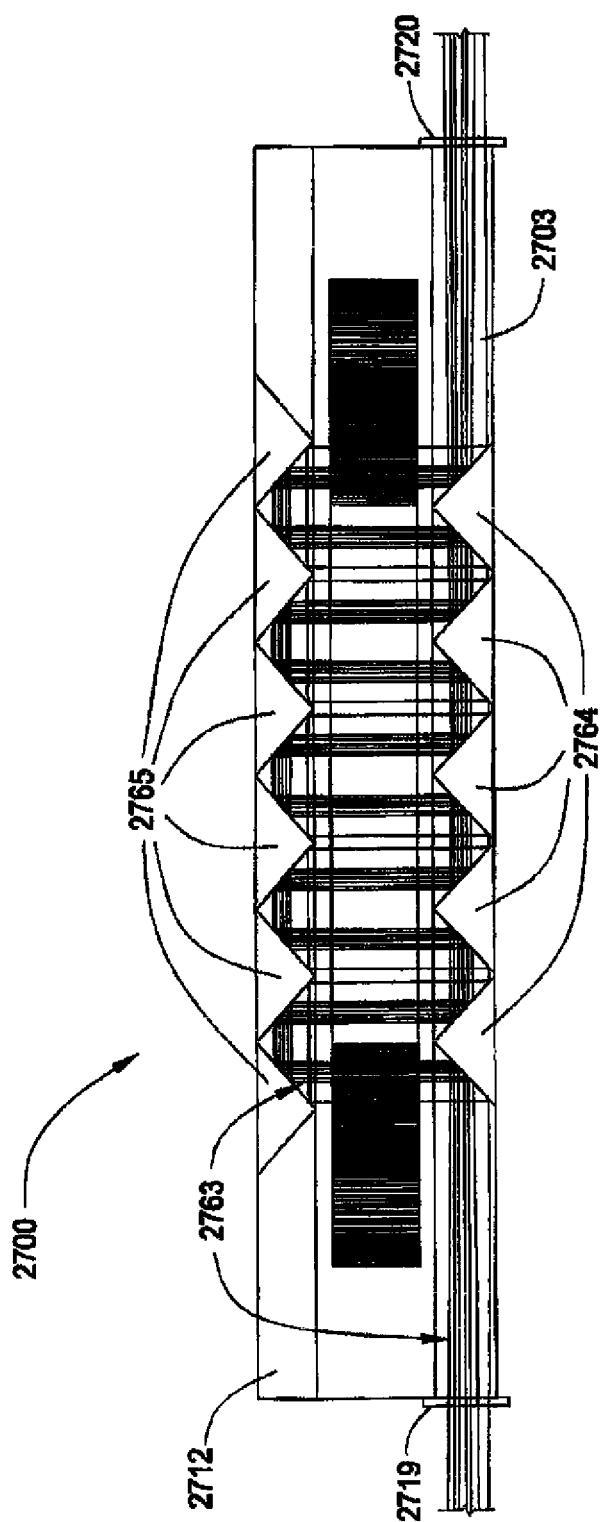
FIG. 25 illustrates a cross-sectional view of FIG. 26 with a ray trace resulting from TIR traversing the optical chamber more than twice.
Figure 26:
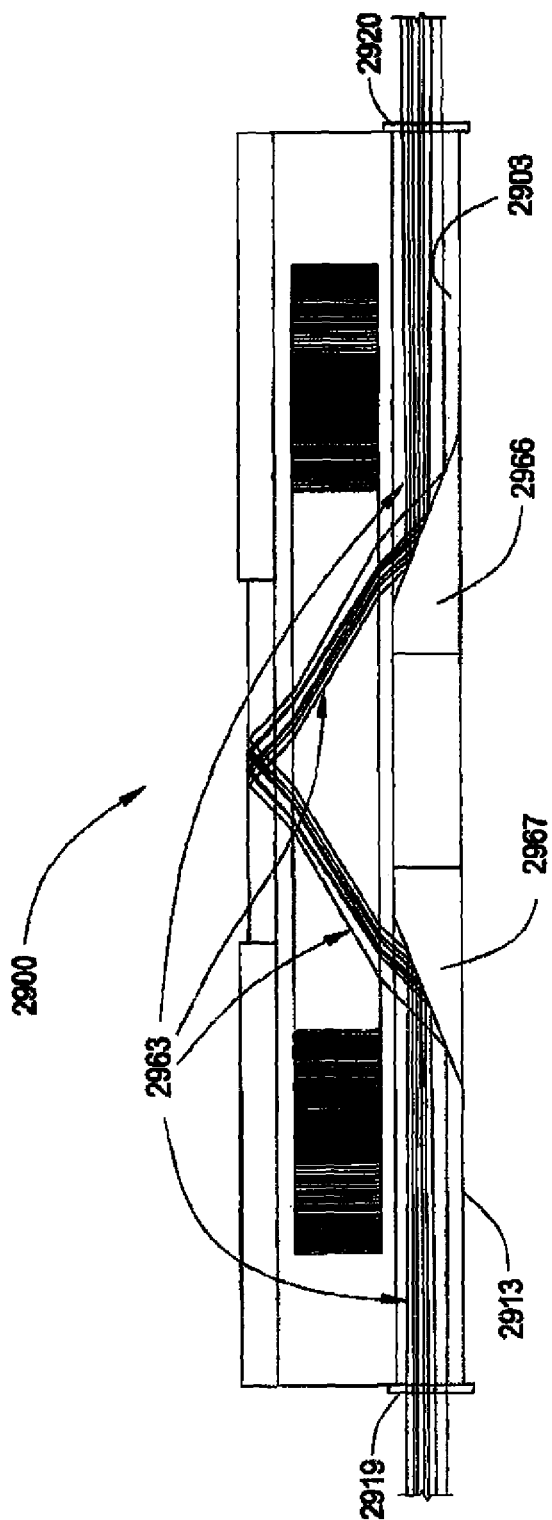
FIG. 26 illustrates a cross-sectional view of FIG. 28 with a ray trace resulting from TIR traversing the optical chamber twice.
Figure 27:
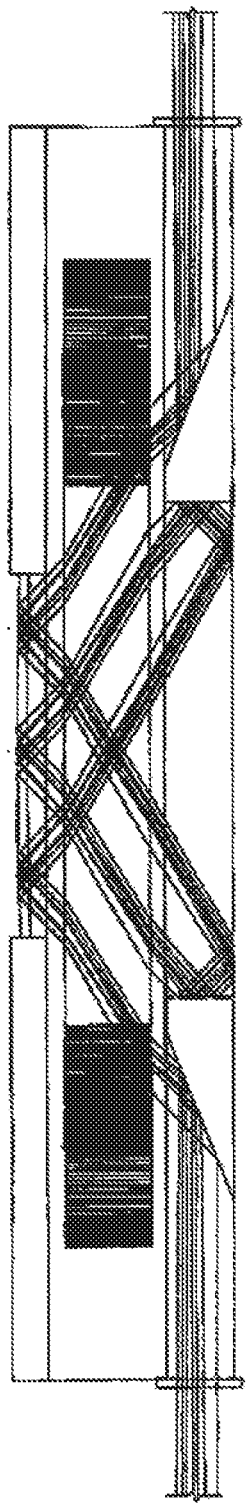
FIG. 27 illustrates a ray trace resulting from TIR and refraction traversing the optical chamber more than twice and including a means to converge light to within the optical chamber.

The concepts depicted in FIG. 22 through 24 can be expanded, as illustrated in FIGS. 25-28, by incorporation of additional internal reflecting surfaces. Any number of transitions may be used. In practice, the greater the number of transitions incorporated, the more sensitive the path length becomes to variation in channel thickness and the greater the losses in the light transmitted through the micro-fluidic cuvette due to scatter, an increase in the focal ratio of the micro-fluidic cuvette and the losses accrued due to location and angular errors of optical surfaces within the body and lid. To a large extent the loss due to the increase in the focal ratio can be overcome by modifying the planar internal reflecting surfaces to that of a non-planar or toroidal shape. To like benefit as adding convex surfaces to optical surfaces 2219 and 2220 of micro-fluidic cuvette 2200, modifying some or all of the internal reflecting surfaces to a non-planar or toroidal shape of micro-fluidic cuvette 2200 can be utilized to prevent the light from diverging beyond the extent of the optical chamber 2203 as the light propagates from one end of the optical chamber to the other.

Figure 28:
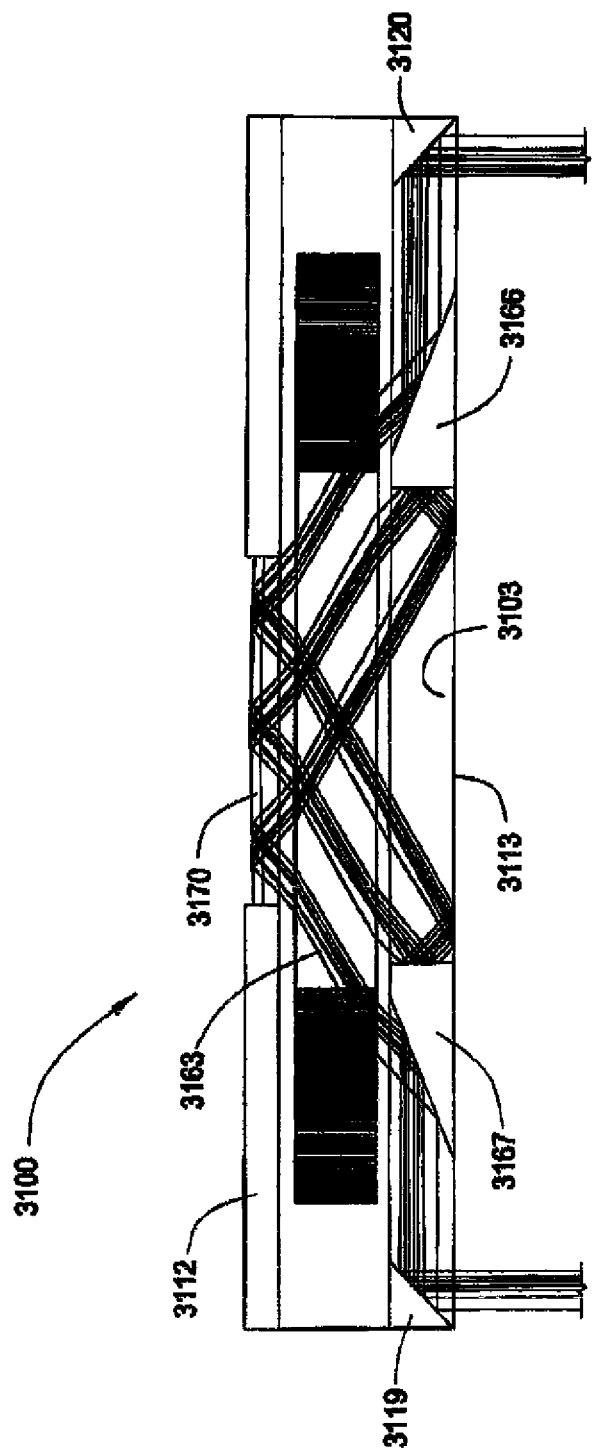
FIG. 28 illustrates a cross-sectional view depicting a ray trace resulting from TIR and refraction traversing the optical chamber more than twice and including a means to confine light to within the optical chamber, including auxiliary TIR optical surfaces.
Figure 29:
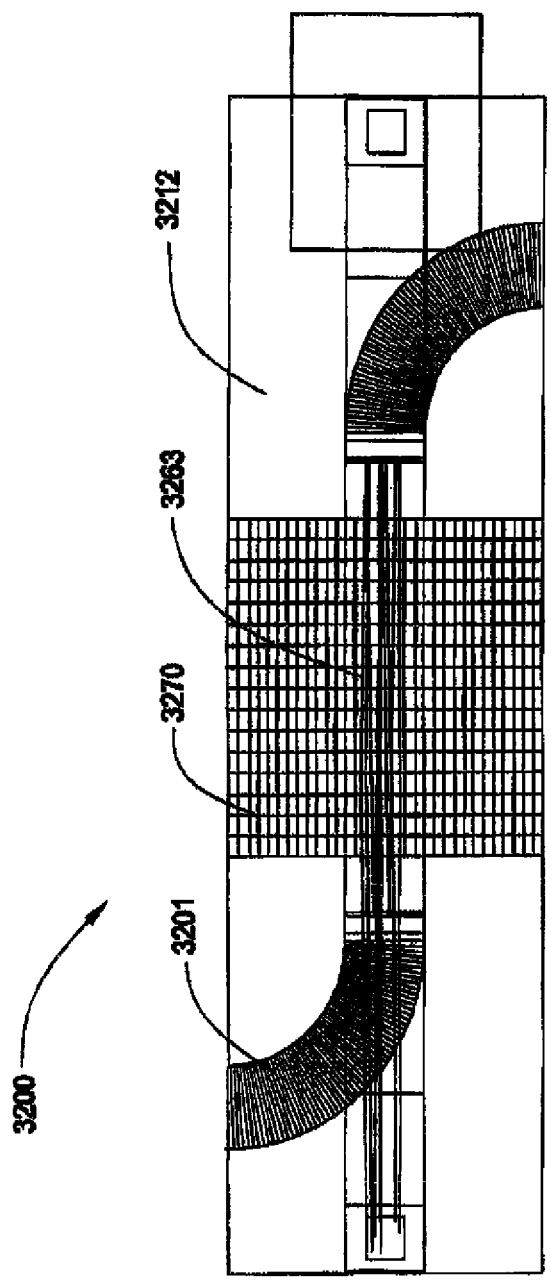
FIG. 29 illustrates a view of an optical feature of a lid of a cuvette.

Auxiliary optical features or modifications to the features of the example cuvette embodiments may be incorporated to form additional embodiments as shown in FIG. 28 and FIG. 29. As example, modification to optical surface features 3119 and 3120 to manipulate the optical axis and/or modification to optical surface 3170 from a planar surface to a non-planar surface is possible. Indeed manipulation of the optical axis can be utilized to accommodate surface mounted emitters and detectors wherein optical surface 3170 of lid 3112 is modified to a non-planar surface to converge rays 3163 as the light propagates within optical chamber 3103 so that light that would otherwise exceed the extent of the optical chamber 3103 for a given focal ratio are not lost. An advantage of modifying optical surface 3170 in lid 3112 as compared to modifying optical surfaces 3166 and/or 3167 of body 3113 to the form of lenses lay in the simplicity of fabrication, reduction in cost and the redundancy of use. Fabrication in such cases does not require complex tooling, decreases the cycle time required to generate the part, increases the feature size and allow for the same optical surface to be utilized for multiple excursions through the optical chamber 3103.

As shown in FIG. 29, modification to optical surface 3270 of lid 3212 reflects rays 3263 impinging upon optical surface 3270 in a manor in which maintains confinement of rays 3263 to within the optical chamber during each excursion of the light through optical chamber.

The detailed descriptions of the above example embodiments of cuvettes are not exhaustive descriptions of all embodiments contemplated. Indeed, persons with ordinary skill in the art will recognize that certain elements of the above-described example embodiments may variously be combined or omitted to create further embodiments, and such further embodiments fall within the scope and teachings of the invention. It will also be apparent to those of ordinary skill in the art that the above-described embodiments may be combined in whole or in part to create additional embodiments.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, including the non-limiting examples provided in the figures, it is to be understood that the embodiments are not limited to those precise example embodiments, and that various other changes and modifications may be affected therein by one skilled in the art without departing from the scope or spirit of the disclosure.

What is claimed is:

1. A method, comprising:
   operating a motor to position sample fluid within a fluid channel of a cuvette, wherein the motor modifies a pressure within the fluid channel to move the sample fluid within the fluid channel;
   transmitting light through an optical chamber of the cuvette, wherein the optical chamber is within the fluid channel;
   measuring a value of received light that has been transmitted through the optical chamber;
   comparing the measured value of light to one or more predetermined threshold values of optical transmission;
   determining a position of the sample fluid within the fluid channel based on a comparison from the comparing step, wherein the determining comprises detecting a leading edge of the sample fluid utilizing slope changes in the measured value of light and a lagging edge of the sample fluid;
   determining a volume of the sample fluid based upon the detection of the leading edge, detection of the lagging edge, and a cross-sectional area of the fluid channel at the position of the sample fluid; and
   generating a response based upon the position of the sample fluid with the fluid channel.

2. The method of claim 1, wherein the one or more thresholds is a threshold derived from light transmitted through the optical chamber and measured prior to operating the motor to position sample fluid within the fluid channel.

3. The method of claim 1, wherein the one or more thresholds is a threshold derived from one or more predetermined standards.

4. The method of claim 3, wherein the one or more predetermined standards comprise one or more of a standard associated with no sample fluid in the optical chamber and a standard associated with a gas/sample fluid interface present within the optical chamber.

5. The method of claim 1, further comprising, responsive to determining a position of the sample fluid within the fluid channel, providing an indication of a detected position, wherein the indication of a detected position is communicated to a user.

6. The method of claim 1, further comprising, responsive to determining a position of the sample fluid within the fluid channel, operating the motor to further position the sample fluid within the fluid channel.

7. The method of claim 1, further comprising, responsive to determining a position of the sample fluid within the fluid channel, calculating a volume of the sample fluid based on the cross-sectional area of the fluid channel and the length which the sample fluid occupies.

8. The method of claim 7, further comprising, responsive to calculating a volume of the sample fluid and determining the volume is an unexpected volume based upon the comparing, providing an indication of the unexpected volume.

9. The method of claim 1, further comprising measuring via the optical chamber one or more optical characteristics of the sample fluid when the sample fluid occupies the optical chamber.

10. The method of claim 1, further comprising iterating the operating, transmitting, measuring and comparing steps in a coordinated fashion with a measured optical characteristic of the sample fluid.

* * * * *